US012708612B2

(12) United States Patent
Streefland et al.

(10) Patent No.: US 12,708,612 B2
(45) Date of Patent: Aug. 18, 2026

(54) COMPOSITIONS FOR DISRUPTING BIOFILM FORMATION AND FOR TREATING BIOFILM-RELATED DISORDERS

(71) Applicant: AHV International B.V., Zwolle (NL)

(72) Inventors: Gerrit Jan Streefland, Arriën (NL); Jan De Rooij, Amsterdam (NL)

(73) Assignee: AHV International B.V., Zwolle (NL)

( * ) Notice: Subject to any disclaimer, the term of this patent is extended or adjusted under 35 U.S.C. 154(b) by 1016 days.

(21) Appl. No.: 17/905,772

(22) PCT Filed: Mar. 12, 2021

(86) PCT No.: PCT/NL2021/050168

§ 371 (c)(1),
(2) Date: Sep. 7, 2022

(87) PCT Pub. No.: WO2021/182958

PCT Pub. Date: Sep. 16, 2021

(65) Prior Publication Data

US 2023/0000811 A1 Jan. 5, 2023

(30) Foreign Application Priority Data

Mar. 13, 2020 (EP) .................................... 20163157

(51) Int. Cl.

| | |
|---|---|
| ***A61K 31/255*** | (2006.01) |
| ***A01N 41/08*** | (2006.01) |
| ***A01P 1/00*** | (2006.01) |
| ***A23K 20/105*** | (2016.01) |
| ***A23K 50/10*** | (2016.01) |
| ***A23L 33/10*** | (2016.01) |
| ***A61K 31/095*** | (2006.01) |
| ***A61K 45/06*** | (2006.01) |
| ***A61P 31/02*** | (2006.01) |
| ***C07C 381/04*** | (2006.01) |

(52) U.S. Cl.

CPC ............ *A61K 31/255* (2013.01); *A01N 41/08* (2013.01); *A01P 1/00* (2021.08); *A23K 20/105* (2016.05); *A23K 50/10* (2016.05); *A23L 33/10* (2016.08); *A61K 31/095* (2013.01); *A61K 45/06* (2013.01); *A61P 31/02* (2018.01); *C07C 381/04* (2013.01); *A23V 2002/00* (2013.01)

(58) Field of Classification Search

CPC ..... A23K 50/10; A23L 33/20; A23V 2002/00; A61P 1/00; A61P 31/00; A01N 41/08; A61K 31/095; A61K 31/255; C07C 381/04

See application file for complete search history.

(56) References Cited

U.S. PATENT DOCUMENTS

| | | | |
|---|---|---|---|
| 5,321,045 A | 6/1994 | Dorsch | |
| 9,339,525 B2 | 5/2016 | O'Neil | |
| 9,770,024 B2 | 9/2017 | Lechado et al. | |
| 9,980,497 B2 | 5/2018 | Gawande | |
| 10,143,198 B2 | 12/2018 | Lechado et al. | |
| 2004/0087665 A1 | 5/2004 | Aubert et al. | |
| 2008/0140036 A1* | 6/2008 | Buck ...................... | A61P 31/04 424/404 |
| 2009/0018194 A1 | 1/2009 | Garcia-Pareja et al. | |
| 2010/0035984 A1 | 2/2010 | Garcia Pareja | |
| 2011/0105623 A1 | 5/2011 | Benjamin | |
| 2012/0171323 A1 | 7/2012 | Bravo | |
| 2013/0079402 A1 | 3/2013 | Bravo et al. | |
| 2014/0303070 A1 | 10/2014 | Bjarnsholt et al. | |
| 2015/0238579 A1 | 8/2015 | Arjona | |
| 2017/0106025 A1 | 4/2017 | Kovarik | |
| 2017/0348253 A1 | 12/2017 | O'Neil | |
| 2019/0374601 A1* | 12/2019 | Bartizal ............... | A61K 9/0073 |

FOREIGN PATENT DOCUMENTS

| | | |
|---|---|---|
| CN | 102731218 | 10/2012 |
| CN | 103037856 A | 4/2013 |
| CN | 106614167 B | 5/2020 |
| EP | 299424 A2 | 1/1989 |
| EP | 1721534 A1 | 11/2006 |
| EP | 2110128 A1 | 10/2009 |
| EP | 2857009 A1 | 4/2015 |
| EP | 3112346 | 1/2017 |
| EP | 3338774 A1 | 6/2018 |
| EP | 3558294 A | 10/2019 |
| EP | 3699171 A1 | 8/2020 |
| FR | 2779615 | 12/1999 |

(Continued)

OTHER PUBLICATIONS

Walker et al., "Coccidioides immitis mastitis in a mare," J. Vet. Diagn. Invest. Jul. 1993;5(3):446-48. PMID: 8373862. (Year: 1993).*

Sorlozano-Puerto et al., Hindawi BioMed Research International, vol. 2018, article ID 7861207, 11 pages.

Rose et al., Nat.Prod.Rep 2005, 22, 351-368.

Rektorisova et al., Plant Foods for Human Nutrition 2020, 75: 376-382.

Olsen, Eur J Clin Microbiol Infect Dis 2015, 34: 877-886.

Mnayer et al., Molecules 2014, 19, 20034-20053.

Abd El-Salam et al., Egypt J Hort. vol. 41 No. 2 pp. 209-219, 2014.

International Search Report issued Jun. 22, 2021 in PCT/NL2021/050168.

Written Opinion issued Jun. 22, 2021 in PCT/NL2021/050168.

(Continued)

*Primary Examiner* — Theodore R. Howell

(74) *Attorney, Agent, or Firm* — ICE MILLER LLP

(57) ABSTRACT

The disclosure relates to thiosulfur containing compositions, in particular propyl-propane thiosulfonate (PTSO) and propyl-propane-thiosulfinate (PTS). Such compositions are useful for treating infection and reducing or degrading biofilms both in vivo and in vitro. In particular, such compositions are useful in the treatment of biofilm-related disorders, including but not limited to mastitis, digital dermatitis, and chronic wound infections.

14 Claims, 6 Drawing Sheets

(56) References Cited

FOREIGN PATENT DOCUMENTS

| | | | |
|---|---|---|---|
| FR | 2947698 | A1 | 1/2011 |
| GB | 2589856 | | 6/2021 |
| KR | 20070035319 | A | 3/2007 |
| WO | 2008037827 | A1 | 4/2008 |
| WO | 2011120182 | A2 | 10/2011 |
| WO | 2012076016 | A1 | 6/2012 |
| WO | 2013124441 | A1 | 8/2013 |
| WO | WO2017152038 | | 9/2017 |
| WO | 2018115532 | A1 | 6/2018 |
| WO | 2022179714 | A1 | 9/2022 |

OTHER PUBLICATIONS

Sheppard, Jordan G., et al., "Allicin-inspired pyridyl disulfides as antimicrobial agents for multidrug-resistant *Staphylococcus aureus*," EP Journal of Medicinal Chemistry, vol. 143, pp. 1185-1195, Oct. 12, 2017.

Clavin-Kouokam, J., et al., "Antimicrobial activity of the essential oil and some isolated sulfur-rich compounds from scorodophloeus zenkeri," Planta Medica, vol. 68, No. 12, pp. 1082-1087, Dec. 1, 2002.

Zhu, et al, "Garlic extract in prosthesis-related infections: a literature review," Journal of International Medical Research 48(4) 1-10, 2020.

Zhu, et al, "Garlic-Derived Metabolites Exert Antioxidant Activity, Modulate Gut Microbiota Composition and Limit Citrobacter rodentium Infection in Mice" Antioxidants 2022, 11, 2033. https://doi.org/10.3390/antiox11102033 p. 1-14.

Ratthawongjirakul et al, "Fresh garlic extract inhibits *Staphylococcus aureus* biofilm formation under chemopreventive and chemotherapeutic conditions," Songklanakarin J. Sci. Technol.38 (4) 381-389 Jul.-Aug. 2016).

Hong Wu et al, "Strategies for combating bacterial biofilm infections," International Journal of Oral Science (2015) 7, 1-7.

Hoiby et al, "ESCMID guideline for the diagnosis and treatment of biofilm infections 2014," Clin Microbiol Infect, ESCMID Biofilm Guideline 2015: 21 S1-S25).

Bochenek et al., "Garlic (*Allium sativum* L.) as an antibiotic alternative determining the hygienic quality of cow's milk from organic farms," Annals of Warsaw University of Life Sciences—Animal Science No. 58 (2) 2019 105-113.

Bastak et al, "Chemical constituents and medicinal properties of *Allium* species," Molecular and Cellular Biochemistry (2021) 476: 4301-4321.

XP028335547 Alireza Khodavandi et al: "Comparison between allicin and fluconazole inbiofilm inhibition and in suppression ofgene expression", Phytomedicine; vol. 19, No. 1 , pp. 56-63.

Ruiz et al, "Garlic derivatives (PTS and PTS-O) differently affect the ecology of swine faecal microbiota in vitro," Veterinary Microbiology, vol. 144, Issues 1-2, Jul. 29, 2010 pp. 110-117.

Abad et al. "Use of Onion Extract as Dairy Cattle Feed Supplement: Monitoring of Propyl Propane Thiosulfonate as Marker of Its Effect On Milk Attributes" J. Agric. Food Chem., DOI: 10.1021/acs.jafc.6b04395 • Publication Date (Web): Dec. 31, 2016.

Vezza, Teresa, et al., "The Immunomodulatory Properties of Propyl-Propane Thiosulfonate Contribute to its Intestinal Anti-Inflammatory Effect in Experimental Colitis," Molecular Nutrition Food Research, vol. 63 (2019).

Vezza, Teresa, et al., "Allium-Derived Compound Propyl Propane Thiosulfonate (PTSO) Attenuates Metabolic Alterations in Mice Fed a High-Fat Diet through Its Anti-Inflammatory and Prebiotic Properties," Nutrients, vol. 13 (2021).

R.M. Abdel-Baky et al., "Inhibition of Urease Enzyme Production and some Other Virulence Factors Expression in Proteus mirabilis by N-Acetyl Cysteine and Dipropyl Disulphide," Advances in Microbiology, Infectious Diseases and Public Health 2017, No. 7, 99-113.

G. Younis et al., "Molecular and Phenotypic Characterization of Antimicrobial Resistance in Gram Negative Bacteria Recovered from Subclinical Mastitis," Advances in Animal and Veterinary Sciences 2017, vol. 5, No. 5, 196-204.

Y. Chen et al., "Allicin Inhibited *Staphylococcus aureus*-Induced Mastitis by Reducing Lipid Raft Stability via LxRa in Mice," Journal of Agricultural and Food Chemistry 2019, vol. 67, 10863-10870.

K. Knapp, "Antimicrobial effects of the organosulfur compounds diallyl monosulphide, diallyl disulphide, and kiallyl trisulphide found in allium sativum against planktonic methicillin-resistant *Staphylococcus aureus* (MRSA) and MRSA biofilms," Senior Independent Study Thesis, 2008, one page abstract.

X. Wu et al., "Analyzing the antibacterial effects of food ingredients: model experiments with allicin and garlic extracts on biofilm formation and viability of *Staphylococcus epidermidis*," Food Science & Nutrition 2015, vol. 3. No. 2, 158-168.

M. Tada et al., "Nematicidal and Antimicrobial Constituents from Allium grayi Regel and Allium fistulosum L. var. caespitosum," Agricultural and Biological Chemistry 1988, vol. 52, No. 9, 2383-2385.

C. Perez-Giraldo et al., "In vitro activity of allicin against *Staphylococcus epidermidis* and influence of subinhibitory concentrations on biofilm formation," Journal of Applied Microbiology 2003, 95, 709-711.

X. Yang et al., "Subinhibitory Concentrations of Allicin Decrease Uropathogenic *Escherichia coli* (UPEC) Biofilm Formation, Adhesion Ability, and Swimming Motility," International Journal of Molecular Sciences 2016, 17, 979.

L. Lin et al., "Effects of Allicin on the Formation of Pseudomonas aeruginosa Biofilm and the Production of Quorum-Sensing Controlled Virulence Factors," Polish Journal of Microbiology 2013, vol. 62, No. 3, 243-251.

* cited by examiner

COMPOSITIONS FOR DISRUPTING BIOFILM FORMATION AND FOR TREATING BIOFILM-RELATED DISORDERS

CROSS-REFERENCE TO RELATED APPLICATION

This application is a Section 371 of International Application No. PCT/NL2021/050168 filed Mar. 12, 2021, which was published in the English language Sep. 16, 2021, under International Publication No. WO 2021/1829581 A1, which claims priority to European Patent Application No. 20163157.9 filed Mar. 13, 2020, the disclosures of which are incorporated herein by reference in their entireties.

FIELD OF THE INVENTION

The disclosure relates to thiosulfur containing compositions, in particular propyl-propane thiosulfonate (PTSO) and propyl-propane-thiosulfinate (PTS). Such compositions are useful for treating infection and reducing or degrading biofilms both in vivo and in vitro. In particular, such compositions are useful in the treatment of biofilm-related disorders, including but not limited to mastitis, digital dermatitis, and chronic wound infections.

BACKGROUND OF THE INVENTION

The health condition of the udder plays an essential role in dairy animals both from a health and wellness perspective as well as from an economic perspective. The infection in mammary glands of dairy animals, such as cows, known as mastitis, has a significant economic impact on dairy farms worldwide. The overall global loss per year is estimated to be four to five billion Euros. In dairy mastitis, the udder is incapable of mounting an efficacious defence response to invading microorganisms. Several factors are known to disrupt the balance at the level of the udder which can compromise the ability of the dairy animal to kill microorganisms causing mastitis. Consequently, host response mechanisms may be incapable of triggering an efficient defence response to eliminate invading pathogens leading to bacterial colonization of the udder and the onset of clinical or subclinical mastitis.

Bacterial colonization and especially the formation of bacterial reservoirs in the udder of dairy cattle are generally difficult to combat, leading to chronic infections that can persist despite certain treatment strategies with or without antibiotics. Important factors associated with the persistence of bacterial infections of the udder in dairy cattle are epithelial adhesion, the production of biofilm and the susceptibility of bacteria to phagocytosis.

Several strategies have been employed in order to control or prevent mastitis in dairy cows, such as antibiotic treatment and vaccination, to name a few, and to reduce the clinical and economic consequences of the disease. However, most treatments and strategies have little or no effect for ameliorating the disease. Several reasons could account for the lack of efficacy. First, although a number of virulence factors have been suggested as potential antigens for single-component vaccines, experimental trials have demonstrated that induction of immunity to single factors is not sufficient to confer robust protection against bacteria causing mastitis in dairy cows. Second, bacterial antigens suffer from low immunogenicity and require adequate adjuvantation. Third, a major challenge in the control of mastitis are effective antibiotics able to reach bacterial pools in the udder for instance as a result of the formation of biofilms by bacteria.

Microorganisms, such as bacteria, do not necessarily need to produce a biofilm, but they have much better possibilities to survive in the host if they can adhere, for instance, to epithelial cells. Adhesion is an active process, involving a series of attachments and detachments, with resulting biofilm formation which is accompanied by significant genetic and subsequent physiological changes in the microorganisms resulting, inter alia, in a loss of sensitivity to virtually all classes of antibiotics. Hence, the management of bacterial udder infections is becoming increasingly difficult due to the emergence and increasing prevalence of bacterial pathogens that are resistant to antibiotics. In some cases, low doses of antibiotics can even enhance biofilm formation suggesting a natural defence mechanism of bacteria in avoiding the lethal effects of antibiotics. Due to this complex and problematic situation, mastitis remains one the most important diseases in dairy cattle despite the progress made in improving general udder health in recent years.

In addition, when cattle are frequently or continuously treated with antibiotics the antibiotics and degradation products are also found in the manure. The manure comprising the antibiotics and degradation products are spread over soil. The presence of the antibiotics is shown to affect the bacterial diversity in the soil. This is an undesirable effect to the environment. An alternative composition to treat infections in cattle will prevent the spread of antibiotics through the environment and recovery of the microbiome of the soil.

Although the description of bacterial biofilms can be found in the scientific literature much earlier, the meaning of biofilms became known in 1982, when Costerton observed that *Staphylococcus aureus* had formed a biofilm on a cardiac pacemaker lead. Subsequent research and clinical observations revealed that bacterial biofilms can be found on implants and catheters, prosthetic devices and other implanted biomaterials. Even more relevant was the observation that microbial biofilms can be formed also on biological surfaces is human and animal tissues such as the periodontal mucosa in the oral cavity (dental plaque), nasal sinuses (chronic sinusitis), the inner ear (otitis media), blood vessels and heart valves (endocarditis), the alveolar surface (multiple lung diseases) or the biliary and urinary bladder.

The first stage of biofilm formation comprises the attachment of cells to a surface. In the second stage, cell multiplication occurs accompanied by the formation of mature structures have many layers of cells. A slime layer is also formed which further protects the bacteria. See, e.g., Melchior et al. Veterinary Journal 2006 171:398-407. Once a critical mass is reached, the outermost cell layer of a biofilm may release 'planktonic organisms'. These organisms may further colonize other surfaces. Biofilms may form on a wide variety of surfaces, including living tissues, indwelling medical devices, industrial or potable water system piping, or natural aquatic systems. As will be understood by a skilled person, not all infections lead to the development of biofilms.

Research in the last 20 years revealed that collective biofilm formation is facilitated by bacterial communication system, denoted as quorum sensing (QS). QS occurs by means of small chemical molecules (so called auto-inducers, AI) permanently excreted by bacteria into their environment. These signalling molecules (for example oligopeptides (AIP) or N-acetyl homoserine lactones (AHL)) are recognized and monitored via specific receptors by other bacteria in their neighbourhood. When a specific density of AIs is reached (a quorum), bacterial cells collectively alter gene expression and either produce virulence factors to attack body cells, or to activate metabolic pathways to form a biofilm at tissue surfaces. Biofilm formation involves the formation of an extracellular matrix consisting of large polymers, initially predominantly polysaccharides, which upon maturation are stabilized by proteins and lipids, resulting in three-dimensional structure.

Once a biofilm infection has been established, it can be very difficult to eradicate. Mature biofilms will intermittently release planktonic cells. This can lead to chronic infections with intermittent exacerbations. While antibiotics or the host's immune response may resolve the symptoms due to planktonic cells, the mature biofilms may remain.

Microbial cells under the protection of a biofilm are often more resistant to antibiotics as well as the body's natural immune responses. Dormant bacteria are metabolically inactive and hence do not express the typical targets of many antibiotics such as synthesis of bacterial cell wall constituents (target for beta-lactam antibiotics such as penicillins and cephalosporins and Vancomycin) and rapid protein (target for Aminoglycosides, Tetracyclines, Macrolides and Linezolid) and DNA synthesis (Fluoroquinolones and Rifampicin) or Folic acid synthesis (Sulfonamides, aminopyrimidines (such as Trimethoprim). Therefore, antibiotic treatment alone is generally not sufficient to eradicate biofilm infections (see also Wu et al. Int J Oral Sci. 2015 March; 7(1): 1-7). While antibiotics may be effective against dispersed (planktonic) bacteria, it is difficult to reach within a biofilm the minimal concentration of antibiotic necessary to eradicate the microorganisms within the biofilm. It has been demonstrated in various in vitro experiments that bacteria growing in a biofilm are 10 to 1,000 times more resistant to various antimicrobial agents when compared to the planktonic bacteria of the same strain (see, e.g., Amorena et al. 1999 J. Antimicrob. Chemother. 44:43-55; Ceri et al., 1999 J. Clin. Microbiol. 37:1771-1776; and Olson et al., 2002 Can. J. Vet. Res. 66:86-92). Olsen et al. reviews various mechanisms of biofilm-induced antibiotic resistance and tolerance (Eur J Clin Microbiol Infect Dis 2015 34:877-886).

For bovine mastitis, this has been reported in a study with field strains of *Staphylococcus aureus* (Melchior, Gaastra & Fink-Gremmels, J. Vet. Med. 2006 53:326-332). The MIC50, Minimum bacterial concentration (BMIC) and MBEC (minimal biofilm eradicating concentration) were determined for 7 strains isolated from mastitis infected cows. Antibiotics tested included those that are commonly used in the treatment of bovine mastitis such as Penicillin, Amoxycillin, Cloxacillin, Cephalothin, Cefoperazone, Cefquinome, Cloxacillin/Penicillin combination, Cloxacillin/Penicillin combination, Lincomycin, Pirlimycin, Tyrosine, Neomycin, Gentamycin, Trimethoprim/Sulfamethoxazole, Florfenicol, and Danofloxacin. For all antibiotics tested the difference between MIC (planktonic bacteria) and MBEC (biofilm eradication concentrations) differed by more than a factor of 256, and very often more than a factor of 2048.

There is also evidence that antibiotics may stimulate biofilm formation. For example, some antibiotics (such as tetracyclines, quinopristine-dalfopristins, and erythromycin) may stimulate the expression of genes (e.g, the ica genes) in bacteria which promotes the adherence of the bacteria (Melchior et al., supra). Interestingly, it has been shown that there is a high prevalence of ica genes among *S. aureus* mastitis isolates (reviewed in Melchior et al., supra). These results support the hypothesis that mammary infections are associated with biofilm formation.

Biofilms can also comprise dormant bacteria. Biofilms employ a number of mechanisms to evade a host's immune response including activating regulators/suppressors that affect immune cell activity and acting as a physical barrier to immune cells (Gonzalez Pathog Dis. 2018 April; 76(3)), but can transit out of dormancy and become active. In general, the immune system only acts against active bacteria and therefore the dormant bacteria can escape the immune system of an individual. Dormant bacteria are able to detach from the biofilm and quickly become active and harmful to the host.

Fungal related biofilms are also known to be more resistant to antifungal drugs as compared to planktonic cells (see, e.g., Fanning and Mitchell PLOS Pathog 2012 8:e1002585 for a review). Accordingly, compounds having antimicrobial effects are not always suited for the treatment or prevention of biofilms.

In a mature biofilm a dormant stage is adopted by down-regulating (gene-shift) of primary metabolism. Dormancy encompasses that biofilm bacteria almost entirely suppress the expression of the typical targets for antibiotics, such as protein and DNA synthesis and cell-wall rebuilding. Subsequently biofilms are inherently insensitive to antibiotics and are often upwards 1000-fold more resistant to them than planktonic (free-floating) bacteria. Furthermore, the higher cell densities found in biofilms considerably increases the probability of horizontal gene transfer, which increases the likelihood of the emergence of strains with increased resistance or altered virulence profiles. The clinical outcome is a phenotypic resistance to common (even modern) antibiotics.

In the protective environment of such a biofilm, bacterial survival time increases. Moreover, the self-constructed inert polysaccharide-rich matrix is non-immunogenic, protecting the biofilm-embedded bacteria from recognition (via PAMPS—pathogen associated molecular patterns) and engulfment by immune cells of the host.

The formation of biofilms can have serious negative consequences in medical, industrial, and natural settings. In particular biofilm-associated infections (i.e., biofilm related disorders) are a serious problem in both humans and animals. Such disorders may be characterized by a chronic inflammatory response with recurrent acute episodes and resistance to antimicrobial therapy and/or host defenses. Wound biofilms delay tissue repair resulting in chronic wounds. It has been suggested that biofilm infections account now for up to 80% of all human microbial infections (Bartell J A et al., 20 Evolutionary highways to persistent bacterial infection. Nature Communications (2019) 10:629 and Sharma et al. 2019 Antimicrobial Resistance and Infection Control 8:76). Jamal et al. reported that the National Institute of Health indicated that 65% of microbial infections and 80% of chronic infections are associated with biofilm formation (Journal of Chinese Medical Association 81:7-11). Biofilms and biofilm-related disorders have been extensively discussed in the literature; see, e.g., Sharma et al. 2019 Antimicrobial Resistance and Infection Control 8:76; Roy et al. 2018 Virulence 9:522-554; and Jamal et al. 2018 Journal of the Chinese Medical Association 81:7-11. Vestby et al. reviews bacterial biofilms and their role in disease (Antibiotics (Basel). 2020 February; 9(2): 59). A comprehensive overview of biofilm infections was presented in 2014 by the European Clinical Society of Microbiology and Infectious Disease, see also David Lebeaux et al. Microbiol. Mol. Biol. Rev. 2014; doi:10.1128/MMBR.00013-14.

For example, *Pseudomonas aeruginosa*, an organism that causes nosocomial infections, forms biofilms on surfaces as diverse as cystic fibrosis lung tissue, contact lenses, and catheter lines. *P. aeruginosa* growing as biofilms have also been found in chronic wounds and can lead to impaired healing of wounds. Biofilms, in particular, *P. aeruginosa* biofilms, also cause chronic infections in the respiratory diseases such as bronchiectasis, chronic obstructive pulmonary disease and in chronic rhinosinusitis. Biofilms formed on medical devices serve as a reservoir of bacteria that can be shed into the body, leading to a chronic systemic infection. *Candida albicans* (a yeast) is the most common fungal biofilm found in hospitals, but is extremely difficult to treat and do not respond well to typical antifungal treatments.

The pioneering studies in bacterial biofilm formation focused on *Staphylococcus aureus* (Gram-positive) and *Pseudomonas aeruginosa* (Gram-negative) because of their involvement in recurrent mastitis in dairy cattle and complicated wound infections. In addition, biofilm formation of *Streptococcus* ssp., avian pathogenic *E. coli* (APEC) and *C. jejuni* biofilm gained attention, as these bacterial species are of public health relevance. Subsequently, other important animal pathogens, including *Actinobacillus pleuropneumoniae* (severe lung infections in swine that might become lethal), *Escherichia coli* (local and systemic infections and systemic septicaemia, which often is a lethal in poultry), skin and enteric diseases in dogs and cats and wound infections and endometritis in horses were recognized as biofilm infections. This list is non-exclusive as biofilm formation is a general trait of almost all micro-organisms.

Accordingly, a need exists for alternative treatments of biofilm-related disorders.

SUMMARY OF THE INVENTION

The disclosure provides the following preferred embodiments.

1. A compound according to formula I

Formula I

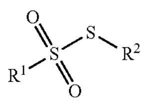

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, or a composition comprising the compound according to formula I, preferably wherein the composition is substantially free of diallyl thiosulfinate, for use in the treatment of a biofilm-related disorder.

2. The compound or composition for use according to embodiment 1, wherein the compound is propyl-propane thiosulfonate (PTSO).
3. The compound or composition for use according to embodiment 1, further comprising a compound for use according to formula II Formula II

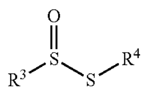

wherein R3 and R4 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula II is not

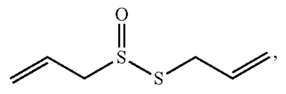

preferably wherein the compound according to formula II is propyl-propane-thiosulfinate (PTS).

4. A compound according to according to formula II

Formula II

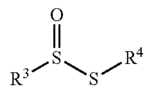

wherein R3 and R4 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula II is not

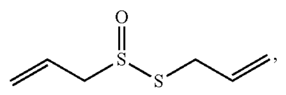

preferably wherein the compound is propyl-propane-thiosulfinate (PTS), or a composition comprising the compound according to formula II, preferably wherein the composition is substantially free of diallyl thiosulfinate, for use in the treatment of a biofilm-related disorder.

5. The compound or composition for use according to any one of the preceding embodiments, further comprising a compound having Formula III Formula III

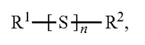

wherein n is 1, 2, or 3 and R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula III is not

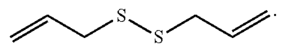

6. The compound or composition for use according to any one of the preceding embodiments, wherein the use further comprises the administration of an antimicrobial agent, preferable selected from an antifungal or an antibiotic.

7. The compound or composition for use according to any one of the preceding embodiments, wherein the use further comprises the administration of an anti-inflammatory agent.
8. The compound or composition for use according to any one of the preceding embodiments, wherein the treatment is for the reduction of biofilm formation or growth and/or for the degradation or reduction of biofilms.
9. The compound or composition for use according to any one of the preceding embodiments, wherein the biofilm-related disorder is a chronic and/or persistent infection.
10. The compound or composition for use according to any one of the preceding embodiments, wherein the biofilm-related disorder is digital dermatitis or a chronic wound infection.
11. The compound or composition for use according to any one of the preceding embodiments, wherein the biofilm-related disorder is an infection of the mammary gland, preferably wherein the biofilm-related disorder is mastitis.
12. The compound or composition for use according to any one of the preceding embodiments, wherein the treatment is for a mammal.
13. The compound or composition for use according to any one of the preceding embodiments, wherein the treatment is for a ruminant, preferably a cow.
14. The compound or composition for use according to any one of the preceding embodiments, wherein the composition is substantially free of diallyl thiosulfinate.
15. The compound or composition for use according to any one of the preceding embodiments, wherein the biofilm comprises bacteria, yeast, fungi, microalgae, or a combination thereof.
16. A method for treating a biofilm-related disorder in an individual, said method comprising administering to an individual in need thereof a composition comprising a compound according to formula I Formula I

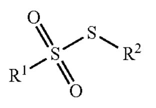

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, preferably wherein the compound is propyl-propane thiosulfonate (PTSO), wherein the composition is substantially free of diallyl thiosulfinate.

17. An article having a surface at least partially coated with a composition comprising a compound according to formula I Formula I

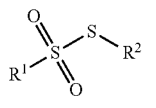

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, wherein the composition is substantially free of diallyl thiosulfinate, preferably, wherein the article is a cleaning product, medical device, or surgical device.

18. An in vitro method for preventing or reducing biofilm formation or growth on a surface or for degrading or reducing biofilms on a surface, said method comprising applying a composition to the surface such as to prevent or reduce biofilm formation or growth on a surface, or such as to degrade or reduce biofilms on a surface, wherein said composition comprises a compound according to formula I Formula I

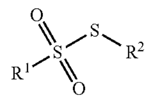

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, wherein the composition is substantially free of diallyl thiosulfinate.

19. A composition comprising a compound according to formula I

Formula I

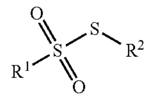

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, wherein the composition is substantially free of diallyl thiosulfinate, and wherein the composition is a pharmaceutical composition or a functional food.

20. The article, method, or composition according to any one of embodiments 16-19, wherein the compound is PTSO.
21. The article, method, or composition according to any one of embodiments 16-20, wherein the composition further comprises an antimicrobial agent, preferable selected from an antifungal or an antibiotic.
22. The article, method, or composition according to any one of embodiments 16-21, wherein the composition further comprises anti-inflammatory agent.
23. The article, method, or composition according to any one of embodiments 16-22, wherein the composition further comprises a compound according to formula II Formula II

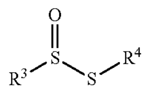

wherein R3 and R4 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula II is not

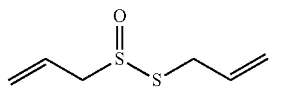

and/or the composition further comprises a compound having Formula III

Formula III

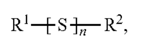

wherein n is 1, 2, or 3 and R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula III is not

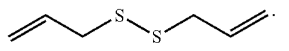

BRIEF DESCRIPTION OF THE DRAWINGS

FIG. 1. Procedure used to measure the effect of QS1 and QS2 on biofilm eradication in the in well measurements of microtiter plates.

DETAILED DESCRIPTION OF THE DISCLOSED EMBODIMENTS

Figure 1A:
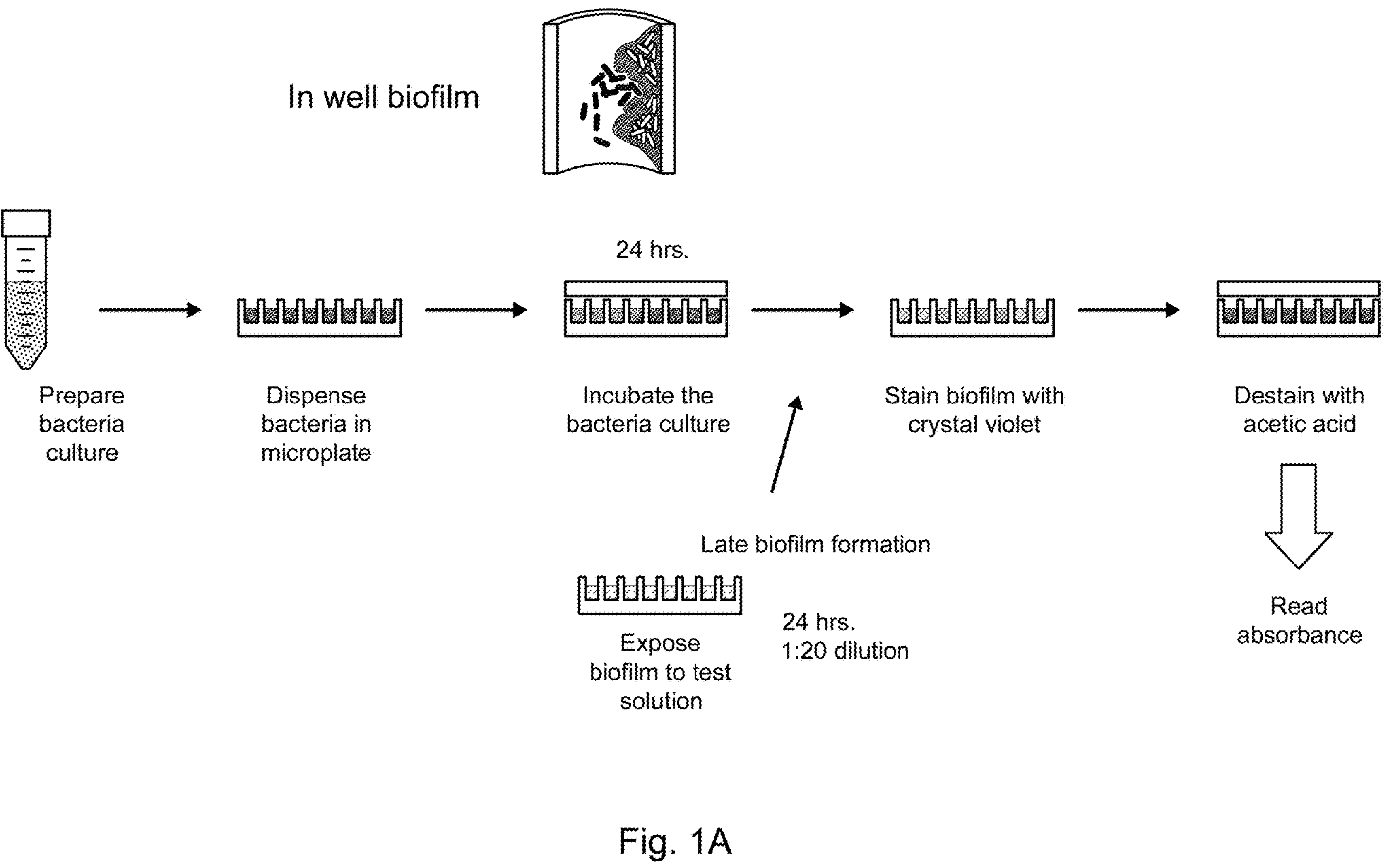
FIG. 1A depicts the method used for measuring biofilms in microtiter plates and FIG. 1B depicts the method for measuring biofilm formation on pegs.

The disclosure provides compounds useful for reducing, degrading, and/or preventing the formation of biofilms. The compounds described herein were surprisingly found to degrade biofilms comprising highly heterogenous microbial populations (see, e.g., Example 2) as well as biofilms comprising known human pathogens (see, e.g., Examples 3 and 4). The disclosure further provides that the compounds are not only active against biofilms in vitro, but also in vivo and can be administered both systemically (e.g., orally) and topically (see, e.g., Examples 5-8).

The disclosure provides a thiosulfonate according to formula I

Formula I

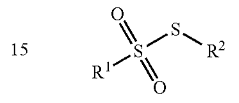

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl.

In some embodiments, the disclosure provides a thiosulfinate according to formula II Formula II

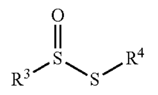

wherein R3 and R4 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula II is not

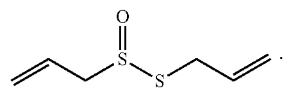

In some embodiments, the disclosure provides a compound having Formula III

Formula III

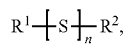

wherein n is 1, 2, or 3 and R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula III is not

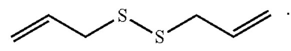

The compounds having formula I, II, or III are referred to herein as, 'the compounds', 'the therapeutic compounds' or 'the therapeutic thiosulfur compounds'. The compounds include salts of formula I, II, or III. Preferably, the compounds have formula I or formula II. Compounds having formula I or formula II may be used together with compounds having formula III. More preferably, the compound has formula I. Preferably, the compound of Formula I is propyl-propane thiosulfonate (PTSO). PTSO has the structure:

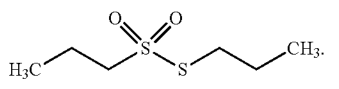

Preferably, the compound of Formula II is propyl-propane-thiosulfinate (PTS). PTS has the structure:

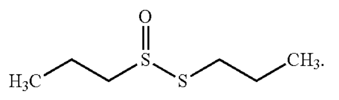

Propyl-propane thiosulfonate (PTSO) and propyl-propane-thiosulfinate (PTS) are natural compounds found in plants belonging to the *Allium* family. For example, *Allium sativum* (Garlic), *Allium cepa* (onion), *Allium ampeloprasum* (leek), *Allium schoenoprasum* (chive) and *Allium chinense* (Chinese onion). The compounds can be either extracted from a natural source or can be produced synthetically. Both compounds PTS and PTSO are also commercially available.

In some embodiments, the compounds are obtained from natural sources such as plants. Compounds can be extracted from plant material in various ways. The appropriate method depends on the chemical properties of the compounds. For example, the extraction can start with a non-polar solvent and follow that with solvents of increasing polarity. Alternatively, the compounds of the plant can be extracted in alcohol. Such extractions may contain e.g., around 80% PTSO and around 20% PTS. In preferred embodiments, the compositions disclosed herein comprise PTSO and PTS at a ratio of at least 3:1, preferably at around 4:1 by weight. While not wishing to be bound by theory, the disclosure provides that the anti-biofilm activities are primarily due to PTSO.

Garlic extracts have previously been described for use in dietary supplements. Garlic is an herb that is grown around the world. It is related to onion, leeks, and chives. Garlic extracts and especially the compounds allicin have been studied for its potential to treat various kinds of diseases. It is most commonly used for conditions related to the heart and blood system. These conditions include high blood pressure, high levels of cholesterol or other fats in the blood, and hardening of the arteries.

For example, Garlicon is a tablet comprising garlic extract. It is described as a garlic powder dried under controlled temperature, in a special dosage form, namely enteric coated tablets. This coating protects the tablet during the passage through the stomach and dissolves in the small intestine to release the content. Garlicon is presented as to protect from the risk of high serum cholesterol levels and heart diseases. In addition, EP 2110128 discloses the use of Alliaceae derived compounds as natural additive in animal feed as an alternative for antibiotics.

In contrast to garlic extracts which comprise a large number of different compounds, with PTSO being a minor component, the compositions provided herein preferably comprises PTSO at a higher concentration than natural garlic extracts. In addition, while natural garlic extracts contain a large number of different substances, each having a different (sometimes unwanted) effect, the compositions provided herein are useful to provide PTSO without any unwanted side effects of other components in garlic extract. In addition, compositions that are enriched for PTSO allow higher dosing.

For example, garlic extract has a strong odor. When animals are provided with such garlic extracts, these odors are also found in animal products such as milk and eggs. Consumers perceive products having these odors as spoiled and such odors can also influence the taste of such products. In practice, animal products collected while using garlic extract would normally need to be disposed of Ingestion of garlic extract by humans can lead to body odor and bad breath.

In contrast, the therapeutic compounds disclosed herein preferably do not have the negative effects of garlic extract described above. For example, for farm animals this had a large commercial advantage in that the resulting animal products (such as milk and eggs) are suitable for consumers. In some embodiments, the disclosure provides methods comprising administering to an individual in need thereof a composition as disclosed herein, wherein said treatment does not result in body odor, bad breath, the presence of abnormal odors in bodily fluids (such as milk), or in the case of avians, does not result in abnormal odors in eggs, or at least to a lesser extent as garlic extract.

The disclosure provides compositions comprising the compounds as disclosed herein, in particular compositions comprising compounds having formula I and/or compounds having formula II. Preferably, such compositions are substantially free of diallyl thiosulfinate. Diallyl thiosulfinate is better known under the name Allicin. Allicin is an organosulfur compound. When fresh garlic is chopped or crushed, the enzyme alliinase converts alliin into allicin, which is responsible for the aroma of fresh garlic. The allicin generated is unstable and quickly changes into a series of other sulfur-containing compounds such as diallyl disulfide. A single garlic clove has about 5 mg to 18 mg of allicin.

As used herein, "substantially free" refers to compositions comprising less than 5 wt % of diallyl thiosulfinate. In some embodiments the compositions comprise less than 1 wt % of diallyl thiosulfinate, preferably less than 0.5 wt % diallyl thiosulfinate. In some embodiments, the composition comprises a ratio of therapeutic thiosulfur compounds (e.g., PTSO and PTS) to diallyl thiosulfinate by weight of at least 10:1, more preferably of at least 100:1.

The compositions of the present disclosure are also preferably substantially free of diallyl-disulfide. In some embodiments the compositions comprise less than 1 wt % of diallyl thiosulfinate, preferably less than 0.5 wt % diallyl thiosulfinate. In some embodiments, the composition comprises a ratio of compounds having formula I and/or formula II (e.g., PTSO and PTS) to diallyl-disulfide by weight of at least 10:1, more preferably of at least 100:1.

In some embodiments, compositions are provided wherein at least 50%, preferably at least 90% by weight of the active ingredients are compounds according to formula I, II, or III as disclosed herein. In some embodiments, compositions are provided wherein the only active ingredients are compounds according to formula I, II, or III, optionally including further antimicrobial agents and/or anti-inflammatory agents. In some embodiments, compositions are provided wherein at least 50%, preferably at least 90% by weight of the active ingredients are compounds according to formula I or II as disclosed herein. In some embodiments, compositions are provided wherein the only active ingredients are compounds according to formula I or II, optionally including further antimicrobial agents and/or anti-inflammatory agents.

The compounds disclosed herein and compositions comprising same are useful in the treatment or prevention of infection. For example, particular uses are for the treatment or prevention of respiratory infection, bowel infection, breast infection, udder infection, skin infection, bladder infection, ear infection, systemic infection, joint infection, brain infection.

As used herein, "infection" refers to, e.g., pathogenic infections which can lead to disease. In particular, such infections are bacterial or fungal infections. In a preferred embodiment, the infection is a bacterial infection. Bacteria and fungi are found almost everywhere and exist in very diverse forms. Most are not harmful and are actually indispensable for life on earth and essential for plant, animal and human health. For example, the microbiome in the intestines of humans and animals where bacteria and fungi live as symbionts with their host is the so-called gut flora. Also, bacteria are naturally present on the skin, which form part of the immune system. Another example is the soil biology, which for the most part consists of bacteria and fungi. Some bacteria and fungi can cause pathogenic infections, for example in animals, or humans. These pathological infections can lead to disease and illness of the infected individual.

As used herein, "treatment of infection" refers to a reduction in the severity and/or duration of the infection and/or a reduction of the severity and/or duration of symptoms from the infection. Preferably, said treatment results in restoration of the health of an individual. Preferably, the individual has less disease symptoms or for a shorter time. As used herein, "prevention of infection" refers to the prevention of or alternatively delaying the onset of infection or of one or more symptoms associated with infection.

Some microorganisms, such as bacteria, microalgae, fungi, etc., can form biofilms. The compounds disclosed herein are also useful in the prevention or reduction of biofilm formation or growth and/or for degradation or reduction of biofilms. Preferably, the compounds, and compositions comprising same, are useful in the treatment or prevention of biofilm-related disorders.

The term biofilm was initially used in technical and environmental microbiology to describe a community of sessile bacteria and other microorganisms attached to natural or artificial surfaces. The formation of a microbial biofilms is initiated by the colonization of bacteria on a surface to which they attach and produce a slimy film consisting of organic polymers. This primary bacterial film attracts other microorganisms such as algae and protozoa, fungi and protozoa resulting in the formation of a visible multispecies biofilm. Such three-dimensional biofilms are ubiquitous in nature and found on all surfaces that are in contact with water. Of public health concern are microbial biofilms in municipal water supplies and household water pipelines and devices. The efficacy of compounds according to formula I, II, and III on such multispecies environmental biofilms is demonstrated in examples 2 and 3.

As used herein, the term "biofilm" refers to a population of microorganisms that are concentrated at an interface (usually solid/liquid) and typically surrounded by an extracellular polymeric slime matrix. Biofilms may form on living or non-living surfaces and are found in natural, industrial and hospital settings. Biofilms can contain many different types of micro-organisms, e.g. bacteria, archaea, protozoa, fungi and algae. Preferably, such biofilms comprise bacteria, microalgae (such as *Prototheca* spp.) or fungi.

As used herein, "treatment of a biofilm-related disorder", also referred to herein as a "biofilm associated disorder", refers to a reduction in the severity and/or duration of the disorder and/or a reduction of the severity and/or duration of symptoms from the disorder, in particular the symptoms of infection. Preferably, said treatment results in restoration of the health of an individual. Preferably, the individual has less disease symptoms or for a shorter time.

As used herein, "prevention or reduction of biofilm formation or growth" refers to the prevention, delay, or reduction of biofilm formation or growth. As will be understood by a skilled person, such reduction of biofilm formation or growth may slow the growth of biofilms as compared to the growth of untreated biofilms. Preferably, the compositions are useful for reducing biofilm formation or growth. As used herein, "degradation or reduction of biofilms" refers to the elimination, either partially or completely, of a biofilm. As will be understood by a skilled person, after such treatment, planktonic bacteria may still be present.

The compounds disclosed herein may be capable of disrupting the structure of the biofilm, for example the extracellular mucous matrix. In some embodiments, the compounds are useful for inhibiting cell adhesion. In particular, the compounds may prevent the adhesion (without killing bacteria) to a static or live surface of all cell types encountered in microbial biofilms in particular free living microbes.

While not wishing to be bound by theory, the present disclosure proposes that the therapeutic compounds disclosed herein may exert part of their effects by affecting quorum sensing. Quorum Sensing (QS) signalling plays an important role in the control of e.g. the expression of bacterial virulence factors. QS involves the accumulation of signalling molecules in the surrounding environment which enables a single cell to sense the density of the number of bacteria and the signalling molecules, and therefore the bacterial population as a whole, can make a coordinated response. These cell-cell communication systems regulate various functions of the bacteria such as motility, virulence, sporulation, antibiotic production, DNA exchange, and development of more complex multicellular structures such as biofilm. Therefore, the interference with QS signalling systems might offer a new strategy to combat persisting (chronic) bacterial infections. The ability of certain substances, such as naturally occurring compounds that have Quorum Quenching (QQ) abilities can be used as anti-adhesive compounds and as compounds that interfere with biofilm formation.

The compounds disclosed herein are particularly useful for treating biofilm-related disorders, wherein the disorder is characterized by a chronic and/or persistent infection. Persistent infection and chronic infection are often used interchangeably, but are based on different mechanisms. Persistent infections are normally held in check by immune defenses but may be activated when such immune defenses are weakened. Persistent infections are often asymptomatic and become clinically visible only when the immune defense fails to control the pathogen. Although persistent infections are often asymptomatic, a skilled person is well aware of means to detect such persistent infections, including e.g., detecting microorganisms from patient samples (e.g., blood or urine). In a chronic infection, pathogens remain in a group of cells/parts of tissue (e.g., joints or lung tissue). The patient always has symptoms of disease, although these might be milder that in the acute phase of infection.

The most prominent examples of a biofilm disease remain bovine mastitis. Bovine mastitis is the clinical term for infections of the mammary gland of cows and can be caused by multiple pathogens, the most prevalent forms are *Staphylococcus aureus, Streptococcus uberis, Streptococcus agalactia, Streptococcus dysgalactiae* as well as *Serratia marcescens* and other facultative pathogenic Enterobacteriaceae and *Prototheca* spp, the latter considered as an emerging pathogen causing an aggressive, non-curable mastitis in many regions of the world. The invention encompasses treating biofilms comprising such microorganisms with the compounds and compositions disclosed herein.

The examples herein describe the surprising efficacy of PTSO in various field trials in cows demonstrating its broad activity in biofilm infections. Another prominent example of biofilm infection are chronic non-healing wound infections. Digital dermatitis, a known biofilm associated disease in cattle serves as an example for such a delayed wound healing process and was successfully treated with PTSO (see example 7). In some embodiments, the wounds treated by the compound of the inventio comprise, for example, *Staphylococcus aureus*; Streptococci; gram negative bacteria, for example *Treponema* spp., *Escherichia coli, Yersinia pestis, Pseudomonas aeruginosa*; or yeast/fungi, for example *Candida* spp (*albicans*), *Cladosporidium herbarum, Trichosporium, Rhodosporidium*, and *Malassezia.*

It is now generally recognized that biofilm-associated microorganisms cause a large number of infections including endocarditis, osteomyelitis, sinusitis, urinary tract infections, chronic prostatitis, periodontitis, chronic lung infection in cystic fibrosis patients, middle ear infections, and various nosocomial infections, especially those related to all known indwelling devices (catheters, implants). The burden of biofilm-disease is significant and represents a major concern in medical care.

While almost all bacterial species are now known to be able to form biofilms under conditions of stress, in current clinical practice several bacterial and fungal species are of major interest, as the associated infections are almost entirely therapy-resistant even if the non-biofilm, planktonic form of the same species and strains show a very good sensitivity to common therapeutic agents (antibiotic and antimycotics/fungicidal agents).

Examples of pathogens which are of major clinical concern due to their biofilm associated therapy-resistance are listed below:

*Aspergillus fumigatus*—Lung aspergillosis (fungal disease)

*Burkholderia cepacian*—pulmonary cystic fibrosis superinfections

*Candida* spp (Yeast)—mucosal surfaces of the gastrointestinal and urogenital tract

*Gardnerella vaginalis* (urogenital tract)

*Escherichia coli* (multiple organs and septicaemia)

*Pseudomonas aeruginosa* (multiple organs and lung infections including cystic fibrosis)

*Staphylococcus aureus* (multiple tissues and wound infections, nosocomial infections)

*Staphylococcus epidermidis* (multiple tissues and wound infections)

*Stenotrophomonas maltophilia* (chronic respiratory tract diseases).

The treatment of such biofilm-related disorders and biofilm-associated microorganisms is encompassed by the invention.

Microbial biofilms are not only formed by bacteria, but also by other microorganisms, particularly pathogenic fungi (*Aspergillus fumigatus* a major cause of multiple *Aspergillus*-related lung diseases) and yeasts (*Candida* spp) colonizing of mucosal surfaces of the gastro-intestinal and urogenital tract. The most prevalent implant-related biofilms are formed by *Staphylococcus aureus* (MSSA and MRSA), *Candida albicans, Pseudomonas aeruginosa, Klebsiella pneumonia*, and *Enterococcus faecalis. Additionally, microalgae such as, e.g., Prototheca* spp can form biofilms and are a source of disease in humans and animals (Protothecosis).

In some embodiments, the biofilm comprises bacteria selected from one or more of *Treponema* spp, *Yersinia pestis, Staphylococcus aureus, Streptococcus agalactiae, Streptococcus dysgalactiae, Streptococcus uberis, Serratia marcescens, Trueperella pyogenes, Mannheimia haemolytica, Pasteurella multocida, Pseudomonas aeruginosa, Burkholderia cepacia, Streptococcus pneumoniae, Hemophilus influenza, Legionella pneumophila, Fusobacterium necrophorum, Corynebacterium pseudotuberculosis, Streptococcus* spp., *Porphyromonas gingivalis, Pseudomonas aeruginosa, Enterococcus faecalis, Neisseria gonorrhoeae, Escherichia coli, Salmonella enteritidis* and *Pseudomonas aeruginosa*. In some embodiments, the biofilm comprises fungi selected from *Absidia* spp., *Actinomyces* spp., *Aspergillus* spp., *Botrytis* spp., *Candida* spp., *Centrospora* spp., *Cephalosporium* spp., *Ceratocystis* spp., *Chaetoconidium* spp., *Chaetomium* spp., *Cladosporium* spp., *Colletotrichum* spp, *Conidiobolus* spp., *Fulvia* spp., *Fusarium* spp., *Geotrichum* spp., *Guignardia* spp., *Helminthosporium* spp., *Histoplasma* spp., *Lecythophora* spp., *Malassezia* spp., *Nectria* spp., *Nocardia* spp., *Oospora* spp., *Ophiobolus* spp., *Paecilomyces* spp., *Paracoccidioides brasiliensis, Penicillium* spp *Phymatotrichum* spp., *Phytophthora* spp., *Pythium* spp., *Piedraia hortai, Rhizoctonia* spp., *Rhizopus* spp., *Rhodosporidium* spp. *Saccharomyces* spp., *Sclerotium* spp., *Sclerotinia* spp., *Torulopsis* spp., and *Trichophyton* spp. Many medically important fungi, such as *Candida, Aspergillus, Cryptococcus, Trichosporon, Coccidioides*, and *Pneumocystis*, are known to produce biofilms. In some embodiments the biofilm comprises microalgae, e.g., *Prototheca* spp.

In certain embodiments, the bacterial infection or biofilm associated disorder is caused by a Gram-negative bacterium. In certain embodiments, the bacterial infection or biofilm associated disorder is caused by a multidrug-resistant bacterium. In certain embodiments, the bacterial infection is a methicillin-resistant *Staphylococcus aureus* (MRSA)-related infection or a *Staphylococcus epidermidis* (e.g., MRSE) related infection.

In a preferred embodiment the biofilm causing bacteria is *Escherichia coli*, preferably the biofilm infection is recurrent urinary tract infection, catheter-associated urinary tract infection, or biliary tract infection.

In a preferred embodiment, the biofilm causing bacteria is *Pseudomonas aeruginosa*, preferably the biofilm infection is Cystic fibrosis lung infection, chronic wound infection, catheter-associated urinary tract infection, chronic rhinosinusitis, chronic otitis media, bronchiectasis, chronic obstructive pulmonary disease or contact lens-related keratitis.

In a preferred embodiment, the biofilm causing bacteria is *Staphylococcus aureus*, preferably the biofilm infection is Chronic osteomyelitis, chronic rhinosinusitis, endocarditis, chronic otitis media, or of (orthopaedic) implants.

In a preferred embodiment, the biofilm causing bacteria is *Staphylococcus epidermidis*, preferably the biofilm infection is Central venous catheter, orthopaedic implants, or chronic osteomyelitis.

In a preferred embodiment, the biofilm causing bacteria is *Streptococcus pneumoniae*, preferably the biofilm infection is infection of nasopharynx, chronic rhinosinusitis, chronic otitis media, or infection in chronic obstructive pulmonary disease.

In a preferred embodiment, the biofilm causing bacteria is *Streptococcus pyogenes*, preferably the biofilm infection is infection of oral cavity and nasopharynx, recurrent tonsilitis.

Clinical signs of biofilm infections are known to the medial practitioner (see, e.g., Table 1 of Wu et al. Int J Oral Sci. 2015 March; 7(1): 1-7). Such biofilm disorders may lead to chronic infections. The determination of acute versus chronic infection is also known to the practitioner. For example, according to the Mayo Clinic, the occurrence of a yeast infection 4 or more times within a year indicates the presence of a chronic yeast infection whereas the occurrence of two or more bladder infections during a 6-month period indicates the presence of a chronic bladder infection (also referred to as recurrent urinary tract infection).

The most common method to treat a pathological infection of bacteria is the use of antibiotics. Current antibiotics operate primarily through growth-dependent mechanisms and target rapidly-dividing bacteria. However, non-replicative or slower growing bacteria (e.g., dormant persister cells, biofilms) display high levels of antibiotic tolerance and/or resistance contributing to persistent and recurring infection. The compounds disclosed herein are suitable for the use in infections or biofilms comprising antibiotic resistant bacteria, antibiotic tolerant bacteria, and antibiotic persistent bacteria. The compounds disclosed herein are also suitable as a second-line therapy, or rather for individuals that did not response to previous treatment (e.g., antimicrobial treatment) or the disorder returned within e.g., one year or 6 months.

The disclosure further provides the compounds as disclosed herein and compositions comprising same for treating any disorder induced by or relating to biofilms. Disorders induced by or relating to biofilms are well-known to a skilled person. In particular, such disorders are biofilm-related infections. Suitable disorders for treatment include, for example, bacterial prostatitis, bacterial vaginosis, biliary tract infections, chronic sinusitis, chronic lung disease, dental caries, endocarditis, kidney stones, laryngitis, lung infection in cystic fibrosis, gingivitis mastitis, middle ear infections, nosocomial (bloodstream) infections, obstructive pulmonary diseases, osteomyelitis, otitis media, periodontitis, pneumonia prostatitis, rhinosinusitis, sinusitis, tonsillitis, tuberculosis, urinary tract infections, and wound infections. For example, *Mycoplasma bovis* is known to cause udder infection and joint infection. Biofilm-related disorders also include disorders caused by biofilms formed on indwelling devices (e.g., medical implants, catheters, etc.). Generally, such disorders are treated by removing/replacing the implant. In a preferred embodiment the disorder is mastitis. In some embodiments, the disorder is not mastitis. In some embodiments the treatment is not for inflammatory bowel disease and in particular is not colitis.

The compounds and compositions as disclosed herein are also useful for treating and preventing infections of implanted medical devices such as joint prosthesis and heart valves as disclosed further herein.

The compounds of the invention are shown to have an effect in the udder of the cow. This indicates that the compounds can pass the blood-milk barrier. The blood-milk barrier if formed by less-permeable tight junctions between mammary epithelial cells to prevent the leakage of milk. Passing the tight barrier between the blood stream and milk indicates that the compounds can also pass the blood-brain barrier and treat infections of the brain and pass the intestinal epithelium allowing for treatment of biofilm-related disorders systemically. The data from the examples also demonstrates the safety and efficacy in vivo, including pharmacokinetic properties that make the compounds suitable for therapy.

The disclosure further provides the compounds as disclosed herein and compositions comprising same for preventing or reducing a inflammation in response to bacterial infection or biofilms. Inflammation is part of the complex biological response of body tissues to harmful stimuli, such as pathogens, and is a protective response involving immune cells and molecular mediators. A function of inflammation is to eliminate the pathogens.

In a preferred embodiment treatment of an individual with the compounds as disclosed herein or compositions comprising same prevents or reduces a clinical inflammation in an animal, preferably a cow. Preferably the treatment prevents or reduces a (clinical) inflammation of the udder. In another embodiment, treatment of an individual with the compounds and compositions comprising same prevents or reduces a (clinical) inflammation in a human. For example, the treatment prevents or reduces inflammation of the skin, preferably prevents eczema.

While not wishing to be bound by theory, treatment of an individual with the compounds as disclosed herein, or compositions comprising same, reduces biofilm formation or growth and/or causes degradation or reduction of biofilms. Therefore, the individual no longer responds with an inflammatory reaction in the presence of the pathogens. With other words, clearance of the biofilms and pathogens within these biofilms reduces the inflammation response and prevents a clinical inflammation.

During treatment of a biofilm, the microorganisms (such as bacteria and fungi) are released from the biofilm. In some cases, the individual's immune system will respond to the active microorganism. This may result in inflammation of the tissue. The activated immune cells and the inflammatory response can also damage the tissue, for example in the milk gland. Suppression of the inflammatory response may therefore prevent or reduce damage to the tissue. For example, the milk gland is less damaged and the milk production of the cow will recover faster.

Furthermore, after tissue has been damaged and the inflammation has ended, the body starts the repair. The macrophages still present stimulate the production of new blood vessels. They also ensure the attraction of fibroblasts. These fibroblasts ultimately cause the formation of granulation tissue. For example, in the case of treatment of a dairy cow, scar tissue may be formed instead of milk producing tissue. The milk production of the cow may therefore be lower than before the inflammation.

In addition to the compounds described herein, further anti-inflammatory drugs can be administered to suppress the inflammatory response and reduce the tissue damage, for example in the milk gland. In a preferred embodiment, the treatments disclosed herein (both therapeutic and prophylactic) further comprise the administration of an anti-inflammatory agent. Anti-inflammatory agents include, for example, nonsteroidal anti-inflammatory agents (cox/lox inhibitors) such as ibuprofen, paracetamol, aspirin, diclofenac, ketoprofen, tolmetin, etodolac, and fenoprofen.

Natural anti-inflammatory agents such as Curcumin, Ginger, *Spirulina*, Cayenne, Cinnamon, Clove, Sage, Rosemary, Black Pepper, natural aspirins, *Boswellia, Sanguinaria*, and/or Green Tea may also be used. In some embodiments, the methods and uses disclosed herein comprise the combined treatment of the therapeutic thiosulfur compounds disclosed herein with an anti-inflammatory agent. The compounds may be administered together or separately. In some embodiments, compositions are provided comprising the therapeutic thiosulfur compounds disclosed herein with an anti-inflammatory agent.

In some embodiments, the methods comprise administering to an individual in need thereof compositions comprising the compounds disclosed herein, preferably such as to prevent or reduce biofilm formation or growth, degrade or reduce biofilms, and/or treat or prevent bacterial or fungal infection. In some embodiments, the composition can be administered to an individual for the treatment (e.g., therapeutic agent) or prevention (e.g., prophylactic agent) of a disease or disorder or infection. In some embodiments the individual has or is at risk of developing a biofilm-related infection.

The compositions can be administered to any individual, in particular to animals. Preferable, the animal is a ruminant (such as cows and goats), more preferably a cow. In some embodiments, the animal is not a cow. Preferably, the animal is a non-ruminant, such as a monogastric, a rodent, non-human primate, porcine, equine, canine, feline, or avian. In some embodiments the animal is a human. In some embodiments the animal is a non-human animal. In some embodiments, the animal is not an aquatic animal such as fish, mollusks, and crustaceans. Preferably, the animal is a mammal or bird.

While not wishing to be bound by theory, the disclosure provides that the compositions disclosed herein can have advantageous effects after a single administration. In a preferred embodiment, effects are achieved by providing a single oral administration of the composition disclosed herein. Such oral dosing may be, e.g., as a tablet which provides an extended release of the compounds disclosed herein.

The disclosure also provides for multiple administrations. For example, the compositions may be provided more than once per day, daily, weekly, or monthly. In an exemplary embodiment the composition may be provided once daily for a week or until symptoms are alleviated.

Actual dosage levels of the pharmaceutical preparations described herein may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compound, the route of administration, the time of administration, the rate of excretion of the particular compound being employed, the duration of the treatment, other drugs, compounds and/or materials used in combination, the age, sex, weight, condition, general health and prior medical history of the patient being treated, and like factors well known in the medical arts. A physician or veterinarian having ordinary skill in the art can readily determine and prescribe the effective amount of the pharmaceutical composition required.

In some embodiments, ruminants, in particular cattle are provided with at least 1 gram of the compounds disclosed herein, preferably at least two grams, and more preferably at least 5 grams. In some embodiments, a ruminant, in particular cattle, are provided with at least 3 g of PTSO. Compositions comprising the compounds for ruminants are preferably provided as an oral tablet.

It is clear to a skilled person that lower amounts of the compounds can be administered to smaller ruminants, e.g., goats. The examples describe the administration of a tablet to cows that comprises 3.84 g PTSO plus 0.96 gram PTS. As the average weight of a cow is around 650 kg this corresponds to a dosage of around 5.9 mg/kg PTSO and 1.5 mg/kg PTS. A skilled person is aware that as smaller animals have higher metabolic rates and thus smaller animals require a larger drug dose on weight basis. Dose conversions between animals, and between humans and animals, are reviewed in Nair and Jacob (J Basic Clin Pharm. March 2016-May 2016; 7(2): 27-31) and Holliday, et al., (1967 The Relation of Metabolic Rate to Body Weight and Organ Size. A Review. Pediat. Res. 1: 185-195).

In some embodiments of the methods and uses disclosed herein, at least 5 mg/day of compounds disclosed herein are provided to a human (such as by oral administration). Preferably, at least 10 mg/day of the compounds are provided. In some embodiments, PTSO is provided to a human at a dose of between 0.1 mg/kg to 100 mg/kg. Such amounts of the compounds are particularly useful when providing the compounds systemically (e.g., orally). A skilled person will recognize that lower amounts can be used when administered locally (e.g., on the skin, gums, wound). The compositions disclosed herein are preferably provided for at least one week or until symptoms are alleviated. While such compositions may be provided several times (e.g., one a week, once a month, twice a year, etc.), prophylactic and therapeutic effects are observed after a single use.

In some embodiments, a composition is provided comprising the compounds as disclosed herein together with one or more additional agents, such as, antibiotics (e.g., antibacterial agents, antiviral agents, anti-fungal agents), anti-inflammatory agents, anti-pyretic agents, and pain-relieving agents.

In some embodiments, the compounds disclosed herein are used together with an antimicrobial agent such as antifungal drugs or antibiotics. While not wishing to be bound by theory, the disclosure provides that the compounds disclosed herein target the biofilms. The antimicrobial drugs can then exert their effect on remaining planktonic cells as well as the microbial cells in the disrupted biofilm. As a skilled person will appreciate, the combination of an antimicrobial with the compounds described herein can reduce the dosage and/or dosage frequency of the antimicrobial.

Exemplary antimicrobials which may be used in the combination treatment include antifungals such as miconazole, ketoconazole, econazole, terbinafine, ciclopirox, tolnaftate, sertaconazole, sulconazole, amphotericin b, chloroxylenol, clioquinol, butenafine, naftifine, nystatin, and clotrimazole. Exemplary antibiotics include Penicillins, Tetracyclines, Cephalosporins, Quinolones, Lincomycins, Macrolides, Sulfonamides, Glycopeptides, Aminoglycosides, and Carbapenems.

The disclosure provides compositions comprising a compound disclosed herein (in particular a compound of formula I) together with an antimicrobial. As a skilled practitioner will appreciate, the compound and an antimicrobial may also be provided separately. In some embodiments the compound and an antimicrobial therapy overlap. In some embodiments, the therapy with a compound of the invention precedes antimicrobial therapy.

In some embodiments, the compositions disclosed herein are provided as or in a food product or a functional food product. The term "functional food" as used herein, refers to those foods that are prepared not only for their nutritional characteristics, but also to fulfil a specific function, such as improving health or reducing the risk of contracting diseases. Such functional foods may also be referred to as dietary supplements or (animal) food additive. To this end, biologically active compounds, such as minerals, vitamins, fatty acids, bacteria with beneficial effects, dietary fibre and antioxidants, etc., are added thereto. Such food products may be in any form suitable for oral consumption, e.g., in the form of a liquid, gel, powder, pill, tablet, or in gel capsules.

The functional food may also include animal digest, e.g., any material that results from chemical and/or enzymatic hydrolysis of clean and undecomposed animal tissue. The functional food may also include dried brewers yeast, e.g., the dried, inactive agent that is a byproduct of the brewing industry. The animal digest and dried brewers yeast have been found to enhance the palatability of the functional food. When present in the functional food, the animal digest comprises from about 10% to about 90% of the functional food and the dried brewers yeast comprises from about 1% to about 30% of the functional food.

In an exemplary embodiment, the disclosure provides a composition comprising pectin, *yucca*, vitamin E, calcium carbonate, probiotics, plant extracts, herbs and oregano. Preferably said composition comprises around 1 to 5 grams of the therapeutic thiosulfur compounds. Said composition is suitable as a tablet, in particular for the treatment of cows. As described in the examples, the composition is suitable for reducing the cell count in milk and for treating mastitis.

In some embodiments, the disclosure provides compositions comprising the therapeutic thiosulfur compounds as disclosed herein together with at least one pharmaceutically acceptable carrier, diluent and/or excipient. (See e.g., Remington: The Science and Practice of Pharmacy, Alfonso R. Gennaro (Editor) Mack Publishing Company, April 1997). As used herein, the term "pharmaceutically acceptable" refers to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio. Furthermore, the term "pharmaceutically acceptable diluent or carrier" refers to a pharmaceutically acceptable material, composition or vehicle, such as a liquid or solid filler, diluent, excipient, solvent or encapsulating material, involved in carrying or transporting the peptide from one organ, or portion of the body, to another organ, or portion of the body.

The pharmaceutical composition may be administered by any suitable route and mode. As will be appreciated by the person skilled in the art, the route and/or mode of administration will vary depending upon the desired results. The pharmaceutical compositions may be formulated in accordance with routine procedures for administration by any routes, such as parenteral, topical (including ocular), oral, sublingual, transdermal, or by inhalation. Parenteral administration includes, e.g., intravenous, intramuscular, intraarterial, intracoronary, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Preferred routes are oral or topical administration.

The compositions may be in any suitable forms, such as liquid, semi-solid and solid dosage forms. The compositions may be in the form of tablets, capsules, powders, granules, lozenges, creams or liquid preparations (in particular for administration to the skin or eye), such as sterile parenteral solutions or suspensions or in the form of a spray, aerosol or other conventional method for inhalation. The pharmaceutical compositions of the present invention include those suitable for oral, nasal, topical (including buccal and sublingual), rectal, vaginal and/or parenteral administration. In particular embodiments, the composition is a topical composition in the form of a cream, gel, ointment, lotion, foam, suspension, spray, aerosol, or powder aerosol. The compositions are particularly useful for administration to the skin. Suitable compositions also include oral care compositions, e.g., toothpaste, dentifrice, tooth powder, tooth gel, subgingival gel, mouthrinse/mouthwash, artificial saliva, denture product, mouthspray, lozenge, oral tablet, and chewing gum.

The disclosure also provides the in vitro use of the compositions as disclosed herein for preventing or reducing biofilm formation or growth on a surface, and/or for degradation or reduction of biofilms on a surface. Preferably, the methods are for reducing biofilm or biofilm formation on a surface. In some embodiments, the method comprises contacting a biofilm attached to a surface with the compositions disclosed herein. The compositions include, e.g., cleaning or sterilizing compositions.

Any surface may be treated with the compositions disclosed herein so as to coat such surfaces. The surfaces may be, e.g., sprayed, dipped, or soaked in the compositions. A surface includes glass, metal, porous, and non-porous surfaces. It also pertains to exterior and interior and surfaces of equipment that can be contaminated, such as those found in the food industry or the medical equipment found in hospitals and health care facilities, as well as plumbing systems (e.g., sink drain), countertops, building materials, ductwork, clean rooms. A surface also refers to the interior or exterior of pipes, for example drains, as well as swimming pools, tanks (e.g., for aquaculture), purification filters, toilet bowl, sinks, surfaces in the greenhouse. A surface also includes water, such as from a drinking trough.

In some embodiments the surface is of a medical device, such as prosthetics (hip implants, dental implants, prosthetic joint, a voice prosthetic, a penile prosthetic) a mechanical heart valve, a cardiac pacemaker, an arteriovenous shunt, a schleral buckle, catheters (e.g., central venous catheter, an intravascular catheter, an urinary catheter, a Hickman catheter, a peritoneal dialysis catheter, an endrotracheal catheter), tympanostomy tube, a tracheostomy tube, a surgical suture, a bone anchor, a bone screw, an intraocular lens, a contact lens, an intrauterine device, an aortofemoral graft, or a vascular graft. Other infections from medical devices include those from abdominal drains, biliary tract stents, breast implants, cardiac pacemakers, cerebrospinal fluid shunts, contact lenses, defibrillators, dentures, electrical dialyzers, endotracheal tubes, indwelling urinary catheters, intrauterine devices, intravenous catheters, joint prostheses, mechanical heart valves, nephrostomy tubes, orthopedic implants, peritoneal dialysis catheters, prosthetic heart valves, prosthetic joints allosplastic orthopedic devices, tissue fillers, urethral stents, vascular prostheses, ventilator-associated pneumonia, ventricular assist devices, ventricular derivations, ventricular shunts, and voice prostheses.

In some embodiments the surface is of a surgical device, such as clamp, forceps, scissor, skin hook, tubing, needle, retractor, scaler, drill, chisel, rasp, or saw.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

The compounds and compositions disclosed herein are useful as therapy and in therapeutic treatments and may thus be useful as medicaments and used in a method of preparing a medicament. In some embodiments, the disclosure provides methods which are not a treatment of the human or animal body and/or methods that do not comprise a process for modifying the germ line genetic identity of a human being. wherein the cell is not a human germ cell line.

All patent and literature references cited in the present specification are hereby incorporated by reference in their entirety.

The invention is further explained in the following examples. These examples do not limit the scope of the invention, but merely serve to clarify the invention.

EXAMPLES

Several compounds isolated from *Allium* have been studied in vitro in order to determine their effect on bacteria with the aim to develop alternatives for antibiotics. For example, Sorlozano-Puerto et al. (Biomed Research International 2018 Article ID 7861207) describes the antibacterial activity of PTS and PTSO against a large number of human pathogens (212 gram-negative bacilli and 267 gram-positive cocci isolated from clinical samples obtained from 479 different patient) using the recommended standard method (CLSI) to determine the MIC50 and MIC90 values, as well as the MBC50 and MBC90 values (the latter are used to demonstrate a direct bactericidal effect) as measure of antibacterial potency. Data for PTSO and PTS were compared against a range of antibiotics used in clinical practice against such pathogens. Results show that for all bacterial strains, several antibiotics out of the test panel were more effective than PTSO or PTS as indicated by lower MIC values of the antibiotic. Based on these in vitro findings, a skilled person would not consider PTSO or PTS as a useful alternative to common antibiotics in the treatment of bacterial infections.

The in vitro assays described in Sorlozano-Puerto et al. measure growth inhibition of planktonic microorganisms. As will be appreciated by a skilled person, the effect of a compound against planktonic microorganisms is not indicative of the effect of such compounds against a biofilm. This has been demonstrated for a number of antimicrobials as previously discussed herein and is also well-known in the literature. See, e.g., Roy et al. which indicates that bacteria in biofilms have increased resistance against conventional antibiotics by around 1000 fold (2018 Virulence 9:522-554).

In contrast to studies concerned with planktonic microorganisms, the present experiments demonstrate for the first time the effect of PTSO and PTS on biofilms. In such assays media and culture conditions (constant agitation of the plates to induce stress by shear force comparable to what happens in a blood stream) stimulate microorganisms, such as bacteria, to rapidly form a biofilm. Such a biofilm assay can be conducted in two ways: by adding the test compound (e.g., PTSO) from the beginning of the experiment to assess its potential to prevent biofilm formation, or by adding the test compound to a mature biofilm to evaluate the biofilm dissolution effect (corresponding to, e.g., example 2 in which an existing biofilm was treated with PTSO).

The main mechanisms of action of a compound in a biofilm assay is related to either its inhibition of quorum sensing and the following collective gene switch resulting in adhesion of bacteria and the synthesis or to the assembly of extracellular matrix to form the 3-dimensional structure of a biofilm. These mechanisms are entirely different from a pure antibacterial/antimicrobial "killing" effect. If a compound, tested effectively in a biofilm assay, but has no antibacterial effect (such as certain antibodies developed against specific biofilm proteins to destabilize the biofilm structure), then the compound may be combined with an antibiotic to ensure that the bacteria released from the biofilm are killed. This is especially the case if the immune system of the animal is compromised. Ifa substance, such as PTSO, has some antibacterial efficacy (albeit by other mechanisms) this would be a considered as a desirable additional effect in clinical therapy, supporting the eradication of a bacterial population by the innate immune system.

Examples 2-4 describe the effect of compounds of the invention using in vitro biofilm assays. Such assays are quite different from assays such as those described in Sorlozano-Puerto et al. which measure growth inhibition of planktonic microorganisms. The present examples surprisingly demonstrate that compounds of the invention have an effect on biofilm eradication.

Example 1 Isolation of PTSO and PTS

Scope: PTSO and PTS was isolated from a plant extract comprising 56% PTSO and 14% PTS (herein referred to as "PTSO/PTS enriched plant extract").

Study design: the order of elution of compounds according to their polarity is estimated from HPLC and the condition for separation are developed on TLC using heptane and ethylacetate as mobile phase. A flash column with a length of 110 cm and a diameter of 25 cm was packed with 15 kg silica (particle size 40-60 μm from ACROS Organics™) in heptane and the column was allowed to stabilise overnight. Purification was carried out by increasing the polarity gradually from 0% to 40%. The fractions of interest, PTS (=peak 6) and PTSO (=peak 7), both identified by $^1$H-nmr, started to elute after 20 liters use of mobile phase and were collected in 2 liters fraction size. The fractions were separated according to the TLC identification of each compound and the corresponding fraction for each compound (PTS or PTSO) were combined. The solvent was evaporated by rotary evaporator to obtain a purified fraction of PTS (32435-2-A) and 2 purified fractions of PTSO (MHA32435-2-B, MHA32435-2-C) as outlined in table 1.

The required purity of >98% was only achieved with the fraction MHA32435-2-B (=PTSO) while the fraction MHA32435-2-A (PTS) and MHA32435-2-C (=2$^{nd}$ fraction of PTSO) showed a purity <98% and needed further purification individually by a second flash chromatography to obtain the desired purity.

The repurification of PTS (MHA32435-2-A) was carried out by packing a flash column (50 cm length and 20 cm diameter) with 2 kg silica (particle size 40-60 μm from ACROS Organics™), using ethyl acetate and heptane as mobile phase and by increasing the polarity from 0% to 20%. The fractions of interest were collected in 250 ml fraction size, identified by TLC and combined. The solvent was evaporated by rotary evaporator to obtain PTS (EWR32514-01-1) with >98% purity.

The repurification of the impure fraction of PTSO (MHA32435-2-B) was done at the same flash column, using the same mobile phase as for MHA32435-2-A with the difference of 3 kg silica (for packing the column), increasing the polarity from 0% to 30% and the fraction size was 100 ml. The repurification resulted in two fractions (EWR32514-02-1 and EWR32514-02-02) of PTSO with a purity >98% as outline in table 1.

TABLE 1

| Peak 6 and peak 7 purity and % recovery from PTSO/PTS enriched plant extract | | | | | |
|---|---|---|---|---|---|
| Peaks | Weight (gr) | HPLC | $^1$H-nmr | Purity (%) | % Recovery |
| 1st step purification of PTS (peak 6) and PTSO (peak 7) from PTSO/PTS enriched plant extract (992 gr) | | | | | |
| 6 (=PTS) | 64 | MHA32435-2-A | MHA-32435-2-A | 93 | 6 |
| 7 (=PTSO) | 651 | MHA32435-2-C | MHA-32435-2-C | 99 | 86 (from both |
| 7 (=PTSO) | 198 | MHA32435-2-B | MHA-32435-2-B | 72 | fractions) |
| 2$^{nd}$ step repurification of peak 6 and the peak 7 (fr. with 72 purity) | | | | | |
| 6 (=PTS) | 46 | EWR32514-01-1 | EWR32514-01-4 | 99 | 5 |
| 7 (=PTSO) | 123 | EWR32514-02-1 | EWR32514-02-4 | 99 | 82 (from all |
| 7 (=PTSO) | 39 | EWR32514-02-02 | EWR32514-02-5 | 99 | fractions with Purity >98%) |

From this example it is demonstrated that PTSO and PTS were purified up to high purity. Samples with a purity >99% were used as indicated in the examples herein and are referred to as "pure PTSO" and "pure PTS".

Example 2. Biofilm in PBR (Photo Bio-Reactor)

In order to determine the anti-biofilm effect of PTSO, PTS and DPD (dipropyl disulfide), a biofilm was grown under controlled conditions in a glass tube reactor, the PBR. A photobioreactor was used as model system because biofilm formation was clearly visible in the glass tubes. After a mature biofilm was formed, increasing levels of pure PTSO, PTS or DPD were added and the biofilm was removed by titration of pure PTSO, PTS or DPD and the dosages were determined that the biofilm was eradicated. Hereafter, the microbial composition was determined of the biofilm by deep sequencing.

Study Design

Heterotrophic microbial biofilm: a biofilm was cultivated in a 26.5-liter glass photobioreactor (PBR) with a tube length of 37-meter incl. bends (the GemTube RD-25 Glass of LGEM). The PBR was filled with 22 liters of not sterilized medium (Table 1).

TABLE 2

| Composition biofilm cultivation medium | |
|---|---|
| Ion | Concentration |
| Macro-elements | |
| $NH_4^+$ | 0.3 mM |
| K+ | 10 mM |
| Ca2+ | 6.8 mM |
| Mg2+ | 3.1 mM |
| $NO_3^-$ | 18 mM |

TABLE 2-continued

| Composition biofilm cultivation medium | |
|---|---|
| Ion | Concentration |
| $SO_4^{2--}$ | 4.6 mM |
| $PO_4^{3-}$ | 2.4 mM |
| Micro-elements | |
| Fe2+ | 31 uM |
| Mn2+ | 14 uM |

TABLE 2-continued

| Composition biofilm cultivation medium | |
|---|---|
| Ion | Concentration |
| Zn2+ | 10 uM |
| B− | 65 uM |
| Cu2+ | 1.5 uM |
| Mo2+ | 1 uM |

The medium further contained 1 g/l glucose. Inoculation took place by the adding 500 ml ditch water from the Zuidpolder near Delfgauw. Air was pumped in with a rate of 1.0 liter/min: at this setting the medium circulation through the PBR in the medium was as low as possible but there was a stable hold-up to realize medium circulation in the PBR. The PBR was covered with a dark plastic screen to prevent exposure to the light. Incubation took place at 12-18° C. and pH was controlled 5 times per week to 5.2-5.7, once per 1.5 day. After a total dosage of 5 g/l glucose, (after 1 week) a slimy layer (biofilm) was formed that covers the whole inner surface of the glass tube. The medium was replaced by fresh medium without glucose when the biofilm was formed.

PTSO, PTS or DPD were added to the PBR as indicated in the tables. Pure PTSO and PTS were obtained as is indicated in example 1 and stable solutions were prepared in water by sonication of 1000× diluted mixtures. DPD (dipropyl disulfide >98% pure) was supplied by Sigma. After each addition step the biofilm culture was incubated for 24 hours to observe the stability of the biofilm.

The numbers of aerobic, anaerobic/micro-aerophilic and fungal CFU's in the biofilm and supernatant were determined according to standard operating procedures as follows: for aerobic colony forming units per ml (CFU/ml) see https://www.iso.org/standard/53728.html; for the determination of anaerobic CFU's/ml see https://www.thermofisher.com/order/catalog/product/AN0025A#/AN0025A (the plates are incubated in an oxygen-free container) and with respect to the numbers of colony forming unites for fungi see http://edgeanalytical.com/wp-content/uploads/Food_AOAC-997.02.pdf (see Table 2).

The composition of the microbial population of the biofilm was determined using metagenome analysis (Illumina deep sequencing).

Another sample of the biofilm was drawn and a part was stored at minus 80 degrees as inoculum material for further studies. The other part of the biofilm was dissolved by gentle sonification and used to determine the aerobic, anaerobic and fungal numbers of colony forming units as described above. Hereafter it was calculated whether the numbers of colony forming microorganisms in the medium corresponded with the number of microorganisms in the biofilm prior to the treatment. In this way it was calculated whether the microorganisms were killed by the treatments, or that the bacteria remained alive and that only the biofilm was solubilized.

Eradication of the Biofilm by PTSO

Microscopic analysis showed a mixture of fungi, protozoa, and bacteria.

The metagenome analysis demonstrated that the biofilm was composed of a highly mixed population. At least 611 different genera of bacteria were identified. The five most abundant genera and their relative abundance are as follows: *Pseudomonas* 46%, *Acidovorax* 13%, *Burkholderia* 4%, *Achromobacter* 4%, and *Lelliotia* 3%. At least 5 different genera of fungi were identified. The five most abundant genera and their relative abundance are as follows: *Cladobotryum* 5%, *Emiricellopsis* 31%, *Fusicolla* 17%, *Mucor* 37% and *Rozella* 10%.

Addition of PTSO resulted in the disintegration of the biofilm. This could be visualized after the first dosage of 0.05 ul/l PTSO by the release of flocks from the biofilm, whereas at a total dosage of 0.65 ul/l the biofilm became significantly thinner and appears nearly completely degraded at the highest dosage.

In order to investigate whether PTSO has a destabilizing effect of the biofilm or simply kills the microorganisms, samples were drawn from the biofilm before the treatments and samples of the liquid medium were drawn before and after treatment and were inoculated as described above to determine the number of colony forming units. The colony-forming units per ml biofilm and in the supernatant were estimated by plating techniques and are reported in Table 3. Hereafter it was calculated whether the numbers of colony forming microorganisms in the medium corresponded with the number of microorganisms in the biofilm prior to the treatment. In this way it was calculated whether the microorganisms are killed by the treatments, or that the bacteria remained alive and that only the biofilm was solubilized (Table 6).

TABLE 3

Released cell numbers during solubilization of a heterotrophic grown biofilm after addition of various dosages of PTSO. The numbers of aerobic, anaerobic/micro-aerophilic and fungal CFU's were according to the standard operating procedure as described herein.

| Day | Dose (ul PTSO/l culture) | Cumulative dosage (ul PTSO/l culture | Aerobic CFU's after 24 hours (×1000) | Anaerobic CFU's after 24 hour (×1000) | Fungal CFU's after 24 hours (×1000) |
|---|---|---|---|---|---|
| 0 | 0 | 0 | 300 | 47 | 18 |
| 2 | 0.05 | 0.05 | 2,033 | 383 | 150 |
| 6 | 0.1 | 0.15 | 3,367 | 750 | 150 |
| 8 | 0.5 | 0.65 | 6,267 | 1,127 | 517 |
| 13 | 1.0 | 1.65 | 17,333 | 4,400 | 20,333 |
| 15 | 2.0 | 3.65 | 5,867 | 2,933 | 1,567 |

Even at the lowest dosage of PTSO, the aerobic, anaerobic/micro-aerophilic and fungal CFU's increase. This indicates that even at low doses, PTSO begins to degrade the biofilm layer with subsequent release of bacteria. At the highest concentration of PTSO, the aerobic, anaerobic/micro-aerophilic and fungal CFU's decrease indicating that at higher doses PTSO has an effect on planktonic microorganisms.

Eradication of Biofilm by PTS

A biofilm was grown as described above. The metagenome analysis demonstrated that the biofilm was composed of a highly mixed population. At least 362 different genera of bacteria were identified. The five most abundant genera and their relative abundance are as follows: *Pseudomonas* 72%, Raoultella 6%, *Flavobacterium* 3%, *Enterobacter* 1.5% and *Acidovorax* 1%.

The visual disintegration of the biofilm was detectable after a total dosage of 11.65 ul/l of pure PTS was added. The solubilization of the biofilm resulted in an increase in CFU's for both aerobic, anaerobic bacteria and fungi in the culture (table 3).

TABLE 4

Released cell numbers during solubilization of a heterotrophic grown biofilm after addition of various dosages of PTS. The numbers of aerobic, anaerobic/micro-aerophilic and fungal CFU's were according to the standard operating procedure as described herein.

| Addition number | dose purified PTS (ul/l) | Total dose purified PTS (ul/l) | Aerobic CFU (×1000) | Anaerobic CFU (×1000) | Fungal CFU (×1000) |
|---|---|---|---|---|---|
| 0 | 0 | 0.0 | 1600 | 453.333 | 14.333 |
| 1 | 0.05 | 0.05 | 600 | 536.667 | 11.667 |
| 2 | 0.10 | 0.15 | 466.667 | 129 | 90 |
| 3 | 0.50 | 0.65 | 1000 | 19.6676 | 23.667 |
| 4 | 1.00 | 1.65 | 1190 | 216 | 25.333 |
| 5 | 2.50 | 4.15 | 1003.333 | 253.333 | 24 |
| 6 | 2.5 | 6.65 | 1566.667 | 290.000 | 19.333 |
| 7 | 2.50 | 9.15 | 1410 | 74.667 | 12.667 |
| 8 | 2.50 | 11.65 | 540 | 59 | 12 |
| 9 | 2.50 | 14.15 | 1430 | 573.333 | 103.333 |
| 10 | 2.50 | 16.65 | 2366.667 | 1033.333 | 223.333 |
| 11 | 2.50 | 19.15 | 2200 | 930 | 273.333 |
| 12 | 2.50 | 21.65 | 1183.333 | 620 | 126.667 |
| 13 | 2.50 | 23.15 | 756.667 | 234 | 59 |
| 14 | 2.50 | 2.,65 | 230 | 109.333 | 12.333 |

Before the first dosage of PTS there was already a certain PTS-dosage independent release of microorganisms from the biofilm, whereas the biofilm was visibly stable. The first measuring at point 0 is likely an artifact. Similar to PTSO, PTS leads to an increase in live microorganisms in the supernatant indicating the degradation of biofilm. At higher doses, the CFU's decrease, indicating that at higher doses PTS has an effect on planktonic microorganisms.

Eradication of Biofilm by DPD

A biofilm was grown as described above. Microscopic analysis showed that the biofilm consists of both fungi and bacteria. No microbial population analysis was performed, because no significant differences were expected with respect to the microbial population of the biofilm.

DPD was added to the culture as indicated in Table 5. During the first 7 doses there was biofilm present in the reactor that visually did not grow or shrink depending on the added doses of DPD. After dose 8, total addition of 167 ul pure DPD/liter culture (=160 mg pure DPD/liter) the biofilm started to release from the glass and dissolved into the medium. This process continued to a total dosage of 317 ul pure DPD/liter pure culture. At higher dosages, only a biofilm spots remained on the glass where the previously thick biofilm was located. Further additions of DPD did not remove the remainder of the thin biofilm.

TABLE 5

Released cell numbers during solubilization of a heterotrophic grown biofilm after addition of various dosages of DPD. The numbers of aerobic, anaerobic/micro-aerophilic and fungal CFU's were according to the standard operating procedure as described herein.

| DPD dose (ul pure DPD/liter culture) | Total dose DPD (cumulative) (ul/l) | Aerobic CFU's after 24 hours (×1000) | Anaerobic CFU's after 24 hour (×1000) | Fungal CFU's after 24 hours (×1000) |
|---|---|---|---|---|
| 0 | 0 | 413333 | 48333 | 31000 |
| 0.50 | 1 | 400000 | 45333 | 33333 |
| 1.00 | 2 | 440000 | 43333 | 29000 |
| 5.00 | 7 | 390000 | 43333 | 35000 |
| 10.00 | 17 | 403333 | 39333 | 25333 |
| 50.00 | 67 | 376667 | 40333 | 24000 |
| 50.00 | 117 | 426667 | 37667 | 22333 |
| 50.00 | 167 | 563333 | 43000 | 18333 |
| 50.00 | 217 | 1766667 | 267000 | 18667 |
| 50.00 | 267 | 1413333 | 340000 | 17000 |
| 50.00 | 317 | 936667 | 100000 | 223333 |
| 50.00 | 367 | 163333 | 35667 | 273333 |
| 50.00 | 417 | 107333 | 19333 | 24333 |
| 50.00 | 467 | 103333 | 9333 | 12667 |
| 50.00 | 517 | 98333 | 5467 | 8000 |

Based on Table 5, it appears that DPD (an exemplary compound having formula III) begins to have an effect on the biofilm after a total dose of around 167 ul/l. At higher concentrations, the aerobic, anaerobic/micro-aerophilic and fungal CFU's decrease indicating that at higher doses DPD has an effect on planktonic microorganisms.

TABLE 6

Total numbers of colony forming units in biofilms before and after treatment by the indicated compounds in the medium of the PBR

| PBR experiment | % volume biofilmin relation to culture volume | Total (released from biofilm) colony forming units/ml (×1000) In biofilm | In culture supernatant |
|---|---|---|---|
| Experiment 1 (PTSO) (heterotrophic enrichment culture) | | | |
| Before start treatment | 18 | 205,000 | 365 |
| 0.9 mg pure PTSO/liter culture | 0 | 0* | 42,000 |

TABLE 6-continued

Total numbers of colony forming units in biofilms before and after treatment by the indicated compounds in the medium of the PBR

| PBR experiment | % volume biofilmin relation to culture volume | Total (released from biofilm) colony forming units/ml (×1000) In biofilm | In culture supernatant |
|---|---|---|---|
| Experiment 2 (PTS) (heterotrophic enrichment culture) | | | |
| Before start treatment | 11 | 36,000 | 2,068 |
| 20 mg pure PTS/liter culture | 0 | 0 | 3,403 |
| Experiment 3 (DPD) ((heterotrophic enrichment culture) | | | |
| Before start treatment | 7 | 52,000 | 493 |
| 208 mg pure DPD/liter culture | 0 | 0 | 3,403 |

0* means: biofilm had disappeared

From the data from table 6 it was surprisingly demonstrated that despite that the variation of the numbers of microorganisms that are detected in the biofilm was high, probably by the high heterogeneity of the biofilm, it became clear that the biofilm eradicating effect of the indicated molecules do not solubilize the biofilm by killing off the microorganisms followed by biofilm solubilization, but by altering the microbial physiology in that way, that only the biofilm was destabilized and solubilized.

Example 3. In Vitro Biofilm Assay

Study Design: biofilm formation was studied with the gram-positive *Staphylococcus aureus* (*S. aureus*) and the gram-negative *Pseudomonas aeruginosa* (*P. aeruginosa*). These specimens are potential pathogens and the biofilm eradicating effects of two PTSO-containing samples were investigated in vitro.

The compositions tested have the following composition:

QS1: 236 mg PTSO/PTS enriched plant extract with 530 mg/liter PTSO and 133 mg/liter PTS was mixed with 250 ml demineralized water.

QS2: 135 mg pure PTSO obtained as is indicated in example 1 and diluted into 250 ml demineralized water by stirring overnight, corresponding to 540 mg/liter PTSO in water.

Figure 1B:
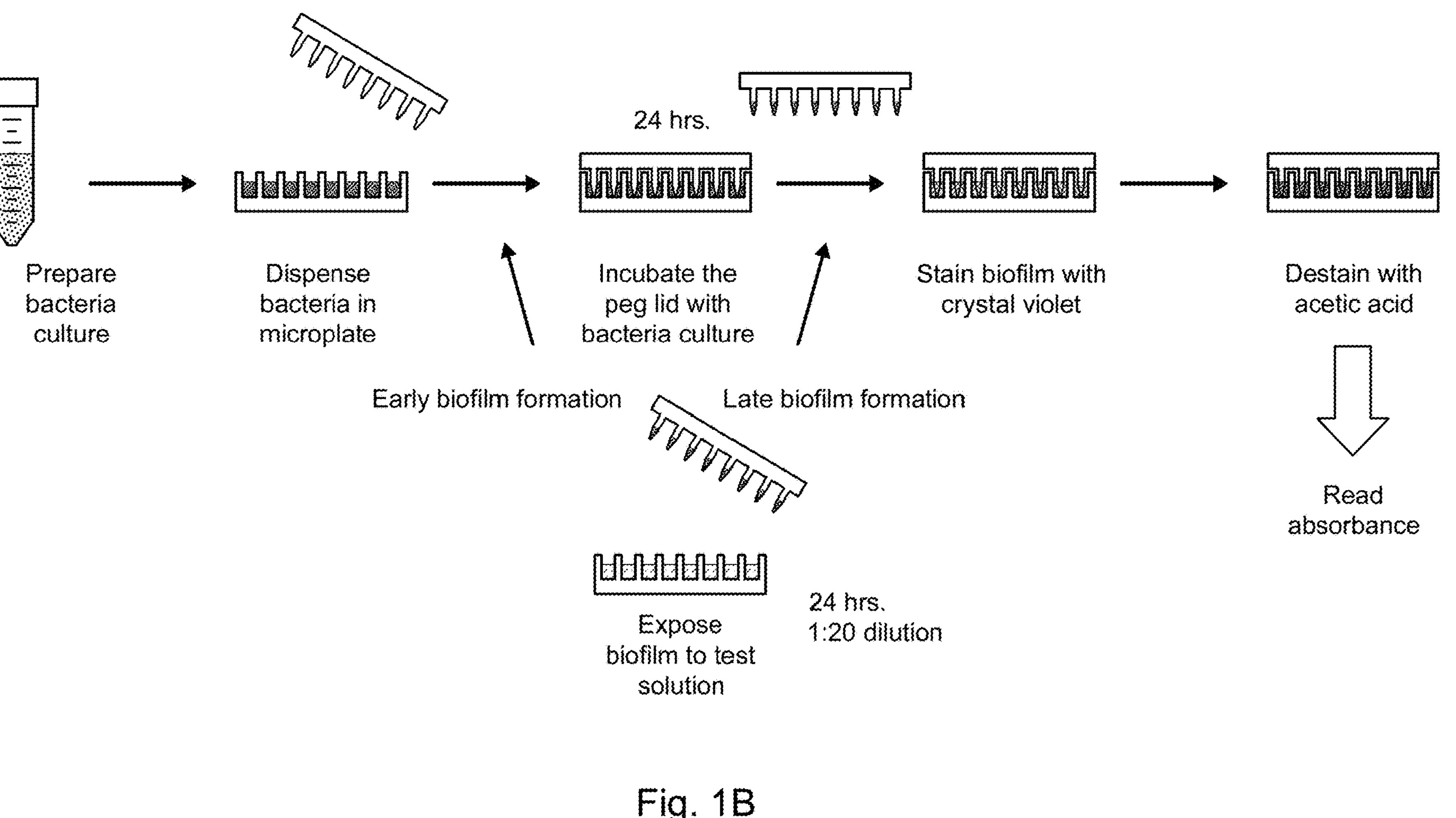
Figure 2A:
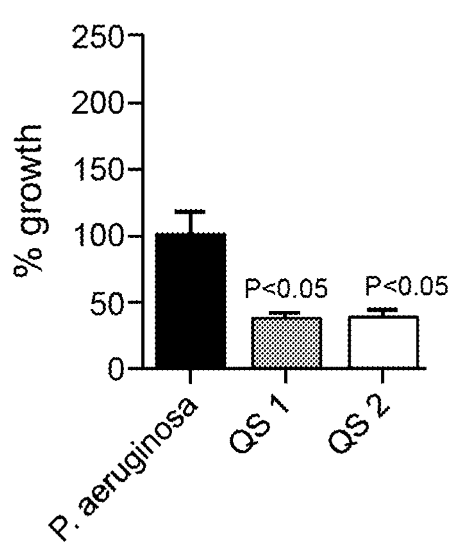
FIG. 2A. The effect of the QS1 and QS2 on late biofilm formation of *P. aeruginosa* and *S. aureus* in rich medium conditions.
Figure 2A:
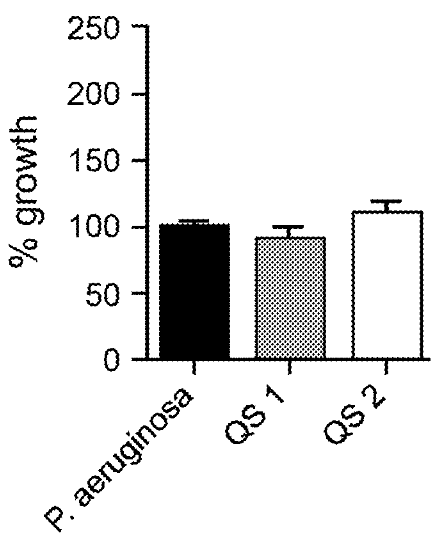
Figure 2A:
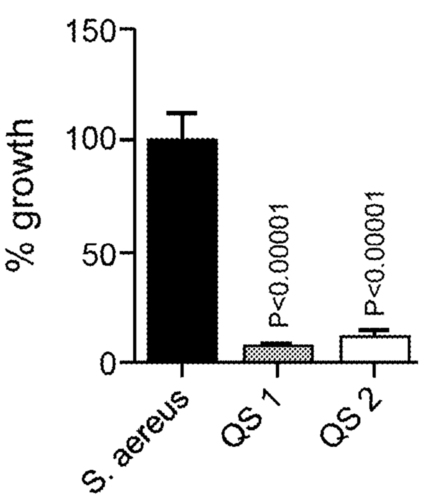
Figure 2A:
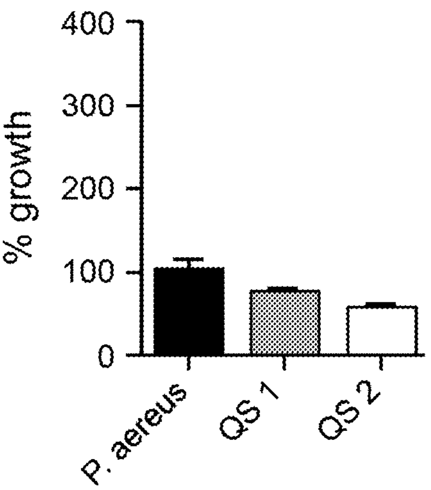
Figure 2B:
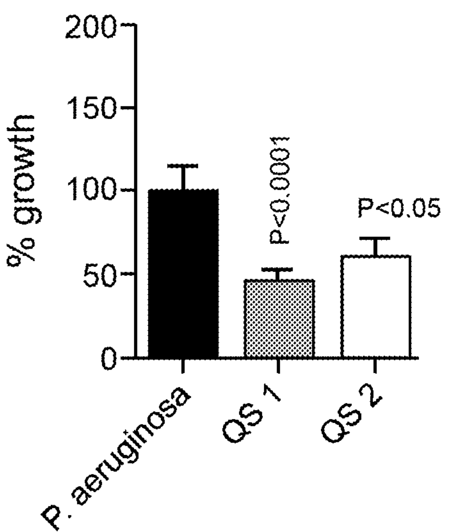
FIG. 2B. The effect of QS1 and QS2 on late biofilm formation of *P. aeruginosa* and *S. aureus* in minimal medium conditions. Left figures: effect on late biofilm formation in wells; right figures: effect on late biofilm formation on pegs. Significance levels are shown as asterisks (*: $P<0.05$; : $P<0.01$; *: $P<0.001$; ****: $P<0.0001$).
Figure 2B:
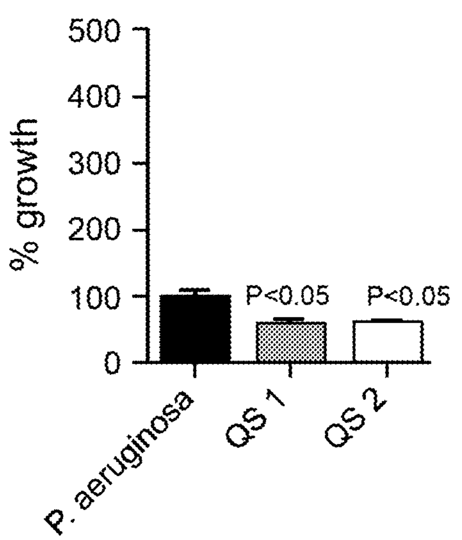
Figure 2B:
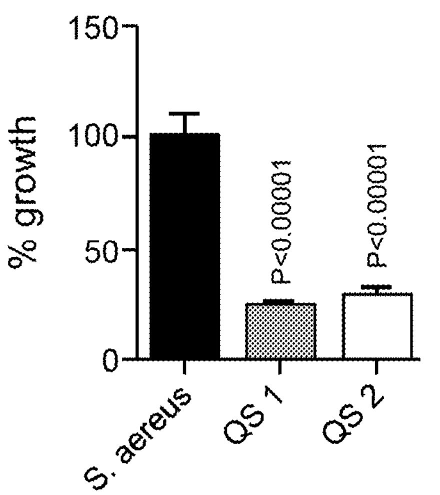
Figure 2B:
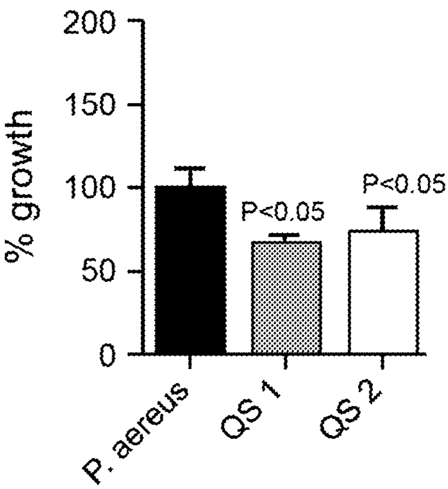

Biofilm formation was studied using the gram-positive *Staphylococcus aureus* ATCC 6538 (*S. aureus*) and the gram-negative *Pseudomonas aeruginosa* ATCC 9027 (*P. aeruginosa*). The experimental method was adapted from ASTM-E2799-17 (Standard test method for testing disinfectant efficacy against *Pseudomonas aeruginosa* biofilm using the MBEC assay ASTM International, West Conshohocken, PA, 2017). In this method *P. aeruginosa* is used and in this example the same test was also applied to test the effects on *S. aureus*. The MBEC (Minimum Biofilm Eradication Concentration) assay is a high throughput screening tool to determine the efficacy of agents against biofilms of a variety of microorganisms. Two methods were used for testing the effect of QS1 and QS2 on biofilms grown in 96 well plates. FIG. 1A depicts the method used for measuring biofilms in microtiter plates and FIG. 1B depicts the method for measuring biofilm formation on pegs.

Briefly, overnight culture of *P. aeruginosa* and *S. aureus* was diluted to 0.1 (OD600). Hereafter, the bacterial suspensions were pipetted into 96 wells plates in a minimal or rich medium in a 1 to 9 ratio. The minimal medium has the following composition: casein, 0.5%; glucose, 2 g/l; $MgSO_4$, 1 mM; $FeSO_4*7H_2O$, 0.5 mg/L. The pH was set at pH 7.3 followed by sterilization. The rich medium contains the following nutrients: casein peptone, 17 g/L; soy peptone, 3 g/L; di-Potassium hydrogen phosphate, 2.5 g/L; sodium chloride, 5 g/L; glucose monohydrate, 2.5 g/L. pH was set at 7.3, followed by sterilization. The 96 wells plates were incubated for 24 hours at 37° C. and a biofilm is formed. Hereafter, the biofilm is exposed to the test solutions as indicated in FIG. 1. Early biofilm formation takes place in the time period 0-24 hours, late biofilm formation takes place in the period 24-48 hours. The suspension is discarded and the wells/pegs are washed with demineralized $H_2O$. Subsequently, crystal violet (0.1%) is added and staining takes place for 15 min; hereafter, washing takes place with demineralized with H2O. Accordingly, the biofilm was destained with acetic acid and transferred to a microtiter plate as was carried out in example 4. The absorbance was measured at 550 nm.

Results and Discussion

The MBEC assay was used to determine the effect of and QS1 and QS2 on biofilm (formation) as shown in FIG. 2. The results are shown as percentage growth (normalized to bacteria without effector 100%); the addition of the word 'peg' (figures) indicates growth on a cone of polystyrene; without 'peg' indicates growth inside a well of microtiter plates. As shown in FIG. 2A (late biofilm formation), growth inhibition was observed in the wells when QS1 and QS2 are added in rich medium for both bacterial specimens. Furthermore, addition of QS1 and QS2 resulted in growth inhibition of *P. aeruginosa* and *S. aureus* in the wells and on the pegs in minimal medium conditions (FIG. 2B).

Based on the biofilm assay (adapted from ASTM-E2799), clear biofilm inhibitory growth effects by QS1 and QS2 were observed with *P. aeruginosa* and *S. aureus*. Biofilms of both bacteria were strongly affected by QS1 and QS2 in the present assay during biofilm formation.

Example 4. In Vitro Biofilm Assay

Scope: as described herein, the effect of a compound against planktonic microorganisms is not indicative of the effect of such compounds against a biofilm. However, in vitro models to study biofilm infections have been developed and results from such models may better predict the effect in vivo. For example, Bahamondez-Canas et al. Biomedicines. 2019 June; 7(2): 34 describes a number of in vitro models for studying wound biofilm infection. In this example in vitro experiments were performed with various strains of the potential pathogenic bacteria *Staphylococcus aureus* and *Streptococcus uberis*, microbial specimens that are involved in mastitis with cows and with respect to *Staphylococcus aureus*, in humans, too.

Study Design:

In this example the following bacterial strains were used: *Staphylococcus aureus* ATCC 25923 obtained from the ATCC collection; *Staphylococcus aureus* 074 was kindly provided by prof Fink, Faculty of Veterinary Medicine, Utrecht University, the Netherlands, described as a clinical isolate from cows with mastitis. Information for the strain is further given in: Melchior, M. B., Fink-Gremmels, J., & Gaastra, W. (2006). Comparative Assessment of the Antimicrobial Susceptibility of *Staphylococcus aureus* Isolates from Bovine Mastitis in Biofilm Versus Planktonic Culture. Journal of Veterinary Medicine Series B, 53(7), 326-332; *Staphylococcus aureus* ATCC 15564 obtained from the ATCC collection and *Streptococcus uberis* clinical isolate from a cow with mastitis, part from the collection of Department of Veterinary Microbiology, Infectious and Parasitic Diseases, Trakia University, Bulgary.

Minimum Biofilm Inhibitory Concentration (MBIC) and Microtiter Biofilm Eradication concentration (MBEC) are defined and measured as indicated in table 7.

TABLE 7

Methods applied for the determination of MBIC 90 and MBEC in this study.

| Parameter | Reference | Definition |
|---|---|---|
| MBIC 90 | Haney E F, Trimble M J, Cheng J T, Vallé Q, Hancock REW. Critical Assessment of Methods to Quantify Biofilm Growth and Evaluate Antibiofilm Activity of Host Defence Peptides. Biomolecules. 2018 May 21; 8(2): 29. | As the lowest concentration that inhibited at least 90% biofilm formation. |
| MBEC | Cruz C D, Shah S, Tammela P. Defining conditions for biofilm inhibition and eradication assays for Gram-positive clinical reference strains. BMC Microbiol. 2018 Nov. 3; 18(1): 173. | The minimal concentration required to reduce biofilm cell numbers below detection limit of the assays used |

Applying the methods as summarised in table 7, the above-mentioned bacteria were tested with PTSO/PTS enriched plant extract, pure PTSO, and pure PTS as described in example 1 and DPD as described in example 2. The results are depicted in the tables below.

TABLE 8

MBIC 90 for *Staphylococcus aureus* strains and *Streptococcus uberis*.

| Bacterial strains | PTSO/PTS enriched plant extract μg/ml | DPD μg/ml | PTSO μg/ml | PTS μg/ml |
|---|---|---|---|---|
| *St. aureus* ATCC 25923 | 64 | >1024 | 128 | 128 |
| *St. aureus* 074 | 64 | >1024 | 128 | 128 |
| *St. aureus* ATCC 15564 | 64 | >1024 | 128 | 128 |
| *Str. uberis* | >64 | >1024 | 128 | 512 |

TABLE 9

MBEC (biofilm eradication) for *Staphylococcus aureus* strains and *Streptococcus uberis*.

| Bacterial strains | PTSO/PTS enriched plant extract μg/ml | DPD μg/ml | PTSO μg/ml | PTS μg/ml |
|---|---|---|---|---|
| *St. aureus* ATCC 25923 | 512 | >1024 | 512 | >1024 |
| *St. aureus* 074 | 512 | 1024 | 256 | 256 |
| *St. aureus* ATCC 15564 | 512 | >1024 | 256 | 256 |
| *Str. uberis* | 256 | >1024 | 512 | 64-128 |

The lowest MBEC values were observed for the PTSO/PTS enriched plant extract, followed by PTSO alone and PTS alone. As data are obtained with a log dilution series, the numerical difference represents only one dilution step. Taken together theses in vitro experiment demonstrated the anti-biofilm activity of compounds of the invention, which is supported by the clinical findings described in the following examples.

Examples 5-8: Treatment of Biofilm-Related Disorders In Vivo

In order to demonstrate the in vivo effects of the compounds disclosed herein, PTSO and PTS were tested on a number of biofilm-related disorders in vivo.

Bovine mastitis is a disease affecting worldwide millions of cows annually. The disease is caused by a variety of very different bacteria and in some cases yeasts that invade the mammary gland of lactating cows, causing a persistent infection and an inflammatory response. Bovine mastitis can be caused various Gram-positive as well as Gram-negative pathogens and the prevalence of individual pathogens may vary to some extent between countries and continents. The most prominent clinical sign of all forms of mastitis is an undesirable increase in the number of somatic cells in the milk intended for human consumption caused by a (chronic) inflammatory response of the udder tissue. This secondary inflammation decreases milk production and hence causes serious economic losses for the farmer. Over the last decades, numerous pharmaceutical products have been introduced into the marked containing different classes of antibiotics, given alone or in combination to treat the primary infectious agents diagnosed as a cause of mastitis. These pharmaceutical products are given systemically (by injection) or locally via the teat channel to fight the bacterial infections. However, despite these great efforts, bovine mastitis remains the most prevalent disease in dairy cow, as antibiotic therapy in generally only temporarily effective and, in many causes, somatic cell counts (SCC), as a clinical marker of mastitis remained high and affected adversely milk yield.

Mastitis is a known biofilm-related disorder. The formation of bacterial biofilms has been demonstrated in in vitro experiments cultivating mastitis pathogen under conditions favoring bacterial biofilm formation (quantifiable after staining and by measuring the genes that drive biofilm formation) as well as in situ by staining the biofilm matrix in the infected bovine udder tissue. For example, FIG. 1 of Schönborn S and Krömker V (2016 Journal Veterinary Microbiology, 30; 196:126-128) which depicts a biofilm matrix from udder tissue from cows suffering from mastitis.

Biomedical research of the last decennia revealed that biofilm formation is not only occurring in cases of udder infection and bovine mastitis but is a general trait of microorganisms invading human and animal tissues and causing persistent infections and inflammation. To date, microbial biofilms are one of the major unresolved challenges in modern therapy of infectious diseases in humans and animals.

Clinical evidence provided in the examples below revealed an unexpected therapeutic effect of PTSO (and to a lesser extent its derivative PTS) in the treatment of important biofilm diseases such as bovine mastitis and infected chronic wounds (e.g., digital dermatitis and UCD). Several field trails are described which demonstrate that the application of PTSO is directly related to a long-lasting stable decrease of somatic cell counts in treated cows, suggesting bacterial cure and tissue regeneration. Further examples describe the effects on biofilm-related chronic wounds (i.e., digital dermatitis and Udder Cleft Dermatitis (UCD).

These findings are remarkable, as it is generally recognized that common antibiotics fail to be effective against biofilm infections. These observations are described in numerous scientific articles from human and veterinary medicine, all suggesting the formation of biofilms as the major cause of recurrent and persistent infections and tissue inflammation and damage. The presented experimental (in vitro) and in vivo (clinical observations) efficacy of PTSO and PTS against prototypical biofilm infections demonstrates that these compounds can effectively be used in clinical practice to prevent and resolve biofilm infections. Biofilm formation and resolution occurs as a direct interaction between the molecules and microbes and is therefore independent of the host (animal or human). As the mechanism involved in biofilm formation are highly conserved between bacterial species, it can be assumed also that the compounds are effective against a broad spectrum of biofilm infections in humans and animals. The examples also demonstrate that PTSO and PTS can be administered orally and exert effects at distinct sites (e.g., mammary glands and claws).

Example 5 Mastitis

Scope

Experiments were performed to examine the effect of a tablet that contains 3.84 g PTSO plus 0.96 gram PTS on the cell count or somatic cell count (SCC) in milk.

The SCC is related with the amount of pathogens that are in the quarter visible for the immune system. The cell count of each cow was measured with the milk production registration (MPR). This MPR is done periodically every 30-40 days at all farms.

The Somatic Cell Count (SCC) is a main indicator of milk quality. The majority of somatic cells are leukocytes (white blood cells)—which become present in increasing numbers in milk usually as an immune response to a mastitis-causing pathogen—and a small number of epithelial cells, which are milk-producing cells shed from inside of the udder when an infection occurs. Inflammation often takes place in one of the udder quarters, resulting in the cell count to rise in this udder. However due to the dilution with the other quarters of the udders the total increase in cell count will be lower. The SCC is quantified as the number of cells per ml of milk. SCC gives an indication of the presence of an (subclinical) udder infection with pathogens causing for instance mastitis and a main indicator of milk quality. The relationship of SCC and mastitis is reviewed in Sharma et al., 2011 Asian-Aust J Anim Sci 24:429-438.

SCC and MPR

The SCC data was extracted from milk production registrations (MPRs). MPRs are databases showing all details (e.g. SCC) of the produced milk per individual cow. MPRs of the selected farms were available periodically every 30-40 days. SCC is quantified as the number of cells per ml of milk. In general terms: an individual cow with a value for SCC of 100,000 or less indicates an 'uninfected' cow and there were no significant production losses due to subclinical mastitis. A threshold SCC of 150,000 would determine whether a cow is infected with mastitis. Cows with a result of greater than 150,000 are highly likely to be infected on at least one quarter. Cows infected with significant pathogens have an SCC of 300,000 or greater.

Examples 5.1

Examination on cell count in 18 cows with the above described tablet.

Examination on cell count in 9 cows with the above described tablet and a comparison with 11 non-treated cows.

Three farms were selected for the study. Table 10 shows information on the size of the farms and the milk produced.

TABLE 10 descriptions of the farms used in Example 5.1

| | Farm 1 | Farm 2 | Farm 3 |
|---|---|---|---|
| Size of farm | 550 cows | 200 cows | 250 cows |
| Number of liters (average per cow per year) | 11.500 liters | 11.200 liters | 8.200 liters |
| Average Percentage of fat in milk | 4.0% | 4.6% | 4.3% |
| Average Percentage of protein in milk | 3.5% | 3.7% | 3.5% |
| Method of milking | Robotic milking | Robotic milking | Robotic milking |
| Access to the outdoors | Yes | Yes | Yes |

Cows with an SCC before treatment of more as 250,000 cells/ml were selected for administration of the tablet. Of each farm the following number of cows were selected:

At farm 1: 6 cows;

At farm 2: 7 cows;

At farm 3: 5 cows.

This resulted in the total of 18 cows.

SCC data was analysed before treatment and in 3 MPRs after treatment.

Results and Discussion

The counts and average somatic cell counts of the milk of the 18 cows are displayed in table 11. After the treatment all cows had a cell count below 150,000 cells/ml at MPR 3. MPR3 is approximately 80-100 days after treatment. A total of 60% had a cell count even lower than 100,000 cells/ml.

TABLE 11

The counts and average somatic cell counts (×1000) of the milk of the 18 cows.

| | cow | Somatic cell counts | | | |
|---|---|---|---|---|---|
| | number | MPR 0 | MPR 1 | MPR 2 | MPR 3 |
| Farm 1 | cow 1 | 385 | 856 | 106 | 45 |
| | cow 3 | 289 | 145 | 148 | 133 |
| | cow 4 | 256 | 85 | 105 | 104 |
| | cow 5 | 304 | 19 | 30 | 32 |
| | cow 6 | 371 | 243 | 59 | 17 |
| | cow 9 | 2354 | 1077 | 507 | 91 |
| Farm 2 | cow 2 | 311 | 45 | 27 | 53 |
| | cow 5 | 361 | 816 | 345 | 119 |
| | cow 6 | 444 | 168 | 356 | 17 |
| | cow 8 | 473 | 126 | 139 | 115 |
| | cow 10 | 265 | 18 | 33 | 131 |
| | cow 11 | 414 | 124 | 623 | 198 |
| | cow 12 | 318 | 507 | 84 | 46 |

TABLE 11-continued

The counts and average somatic cell counts (×1000) of the milk of the 18 cows.

| | cow | Somatic cell counts | | | |
|---|---|---|---|---|---|
| | number | MPR 0 | MPR 1 | MPR 2 | MPR 3 |
| Farm 3 | cow 1 | 3096 | 223 | 19 | 24 |
| | cow 2 | 258 | 25 | 17 | 26 |
| | cow 3 | 580 | 115 | 82 | 51 |
| | cow 5 | 358 | 14 | 9 | 14 |
| | cow 8 | 228 | 107 | 52 | 178 |
| | Average | 615 | 262 | 152 | 77 |

Conclusion

It is shown that the SCC of the milk decreased in the selected cows after treatment with the tablet. It was very surprising because this clearly showed that that PTSO/PTS is absorbed by the intestine, followed by entering the bloodstream. PTSO/PTS was given orally in the mastitis clinical trials described herein. As a clinically significant effect was observed in the udder tissue, this suggest that PTSO/PTS is not only passing the rumen (indicating stability to rumen microorganisms), but also reaches the post-hepatic blood stream (indicating minor or insignificant hepatic biotransformation and inactivation), and ultimately the mammary gland in a concentration that is therapeutically effective. This example that the tablet is reducing effectively the SCC and therefore a good therapeutic effect on udder related infections. Furthermore, all cows showed a lower SCC than 150,000 cell/ml after MPR 3, which indicates the effectiveness on all individual cows in this study.

Example 5.2

For the analysis Farm 1 and Farm 2 were used as indicated below. The cows were selected based on cell count from MRP0 (before treatment). Between 200,000 cells/ml and 500,000 cells/ml the cows were treated or not treated with a tablet that contains 3.84 g PTSO plus 0.96 gram PTS in the same period.

The following number of cows were selected for the cows of the treated group:

Farm 1: 5 cows

Farm 2: 4 cows

The following number of cows were selected for the cows of the not treated group:

Farm 1: 5 cows

Farm 2: 6 cows

For the treated group and not treated group, a 150,000 cell/ml SCC level was selected based on a healthy maximal level of cells in the milk from young cows (heifers). The percentage of cows that are below this level are listed in Table 12. The results showed that the percentage of cows below 150,000 in the treated group increases while the non-treated group is not. The treated group finally reaches 100% after MPR4. The non-treated cows showed a large spread in SCC and did not show any significant decrease in cell count.

TABLE 12

Percentage of cows showing SCCs below 150,000 cell/ml with and without treatment and associated P-value. Not all the cows of the experiments were tested on SCC in each MPR: this is indicated in the final 2 columns.

| | Percentage treated below 150,000 cells/ml (average SCC × 1000) | Percentage not treated below 150,000 cells/ml | P-value | Number of cows tested on SCC | Number of cows not tested on SCC |
|---|---|---|---|---|---|
| MPR0 (before treatment) | 0% (290) | 0% (290) | | 9 | 11 |
| MPR1 | 89% (159) | 36% (431) | 0.028 | 9 | 11 |
| MPR2 | 89% (111) | 18% (322) | 0.005 | 9 | 11 |
| MPR3 | 89% (77) | 33% (212) | 0.050 | 9 | 9 |
| MPR4 | 100% (75) | 29% (320) | 0.021 | 7 | 7 |

Tablet administration to cows with cell counts in between 200,000-500,000 cells/ml was clearly shown effective in reducing the somatic cell count in comparison to non-treated cows.

Example 5.3

The research was conducted on nine farms using milking robots, with a minimal herd size of 80 cows (Holstein). Only cows with an increased SCC were included. Cows are considered to have an increased SCC when over 300,000 cells per milliliter are measured. Cows were in the early stages of lactation until 5 months before the non-lactation period. In this way they could be monitored for a longer period of time.

The SCC data was collected on the basis of MPRs. The cows that were treated with a tablet that contains 3.84 g PTSO plus 0.96 gram PTS were analyzed for the effect on SCC. Hereafter, the data were evaluated for the number of cows that showed a reduction in SCC and the total reduction in cell count. Furthermore, a comparison was made between groups of cows with different lactation stages in case an effect of age was present.

Decrease in SCC after Tablet Administration

The results on the amount of cows showing a decrease in SCC per MPR data set are shown in Table 13. A first MPR after administration of the tablet was available for all 63 cows. For 44 cows, the administration of the tablet effectively reduced SCC. For 42 cows the SCC was under 300,000 cells. A second MPR measurement was available for 48 cows. For 31 cows, SCC was lower than before administration of the tablet. Among which 31 cows showed a SCC under 300,000 cells. The third MPR measurement is only available for 12 cows. Of these 12 cows, 9 cows still had cell counts lower than before the tablet was administered.

Furthermore, the total reduction in cell count was also evaluated. The results of the first MPR are listed in Table 14, the results of the second MPR in Table 15. The results show that the majority of the cows showing a reduction in SCC, are categorized in the group of 100,000-500,000 cells. When the average decrease in SCC before administering the tablet is compared with the average SCC after, the average decrease is 250,000 cells/ml.

TABLE 13

Number of cows with a reduced cell count (SCC)

| | Total no. of cows | No. of reduced | No. of cows < 300K cells |
|---|---|---|---|
| First MPR after tablet | 63 | 44 | 42 |
| Second MPR after tablet | 48 | 31 | 31 |
| Third MPR after tablet | 12 | 9 | 8 |

TABLE 14

Cell count decrease at the first MPR

| Reduced in cells | No. of cows | Percentage |
|---|---|---|
| 0-100,000 cells | 11 | 17% |
| 100,000-500,000 cells | 19 | 30% |
| >501,000 cells | 12 | 19% |
| No effect | 21 | 33% |

TABLE 15

Cell count decrease at the second MPR

| Reduced in cells | No. of cows | Percentage |
|---|---|---|
| 0-100,000 cells | 6 | 13% |
| 101,000-500,000 cells | 17 | 35% |
| > 501,000 cells | 8 | 17% |
| No effect | 17 | 35% |

Lactation Stage

Young cows (first or second lactation stage) may show a more pronouncing effect in SCC decrease after the tablet administration than older animals. Of the 63 cows included in the study, 32 cows are in the first or second lactation (young cows), while the other 31 cows vary from the third until sixth lactation. Of the cows that are in the first or second lactation, 23 cows from the total of 32 cows have decreased cell count levels (72%). For the 31 cows that already have had several lactations, 18 cows have decreased cell count levels (58%). Surprisingly, this indicated that the treatment has a better effect on cows that are in the first or second lactation. For the younger cows the cell counts also remained lower after the second MPR measurement. This clearly shows the efficacy of the PTSO/PTS containing tablet with respect to decrease the SCC, that is considered as an indication of the presence of (subclinical) mastitis.

Example 5.4

The milk of cows with elevated SCC-values were investigated on biofilms that can be selected form the milk as flocs. In the fresh milk of a cow with elevated SCC, flocs were isolated. Samples were prepared for microscopic observation (stained by standard gram staining and crystal violet) and observed by using a NIKON fluorescence microscope. Bacteria were detected. The biofilm was plated out on agar plates and the bacteria were isolated.

For *Staphylococcus aureus,* 100 ul milk sample was plated on Baird-Parker agar with 5% egg yolk emulsion with 3.5% L-tellurite. The plates were incubated at 37 C for 24 hours. Hereafter, a pure culture of the identified *S. aureus* colony was prepared on sheep blood agar. With respect to the isolation of *Streptococcus uberis,* 100 ul milk sample was plated out on sheep blood agar with 10 mg/ml polymyxin and neomycin and incubated at 37 C for 24 hours. A colony was picked up and a pure culture was prepared by various plating on 5% sheep blood agar. The isolated strains were frozen into 1.5 ml TSB (tryptone Soy Broth)-medium plus 20% glycerol. Strain identification was performed by a Vitek2 (Biomerieux Benelux B.V., Amersfoort, The Netherlands). For the preparation of a biofilm, cells were diluted to a concentration of $10^8$ CVE/ml in TSB-medium. 20 ul was transferred to 180 ul TSB medium containing 2 g/l glucose in a 96 wells plate. The plates were incubated at 37 C for 5 days without staking. Hereafter, excess medium was removed and the biofilm was rinsed with excess PBS phosphate buffered saline. The wells were dried on the air and ready for microscopic staining and analysis as described above.

The effect on the milk was monitored in the days after administering of the PTSO/PTS tablet (3.84 g PTSO plus 0.96 gram PTS) to the cow.

Results and Discussion

Microscopic observation of the biofilm isolated from the milk clearly demonstrated the presence of biofilm associated cells. These cells were used to prepare pure cultures and were identified as *S. aureus* and *S. uberis*. Biofilms were then cultivated in vitro. This clearly demonstrated the involvement of biofilms with respect to mastitis infections.

Figure 3A:
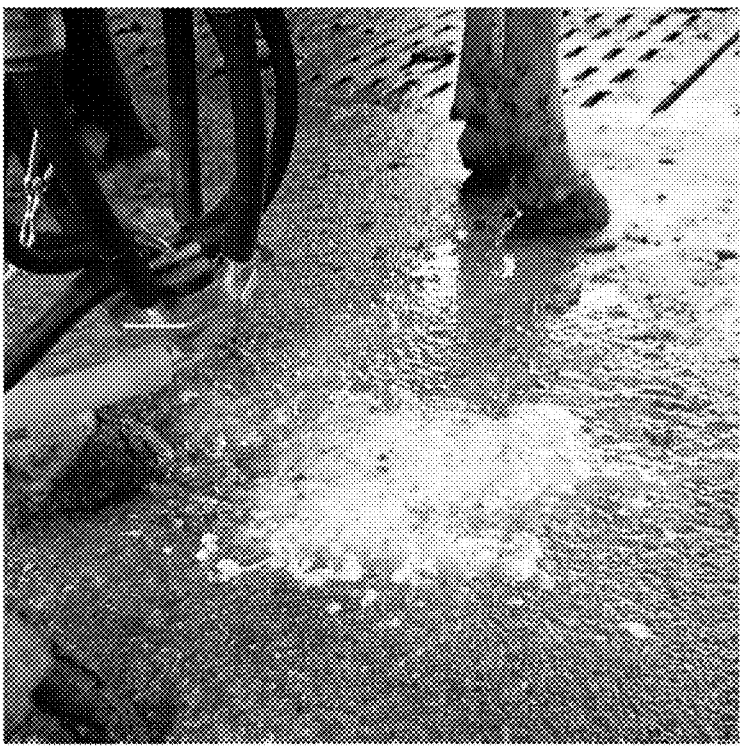
FIG. 3 (A). Biofilm that was released directly out of the udder after milking; (B) biofilm that was obtained after sieving of milk after milking of a cow with mastitis, one to three days after treatment with the PTSO/PTS tablet.
Figure 3B:
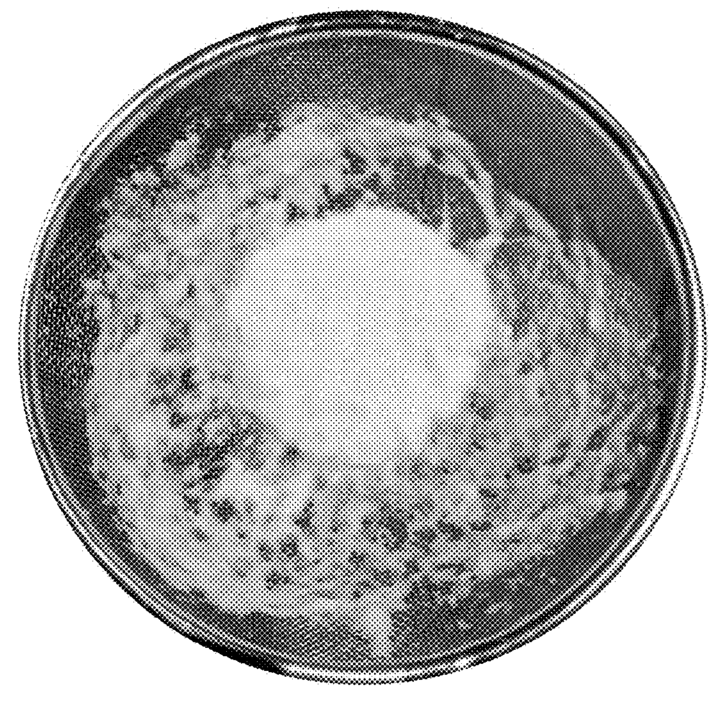

Shortly after administering the cow with a PTSO/PTS tablet, the milk from the treated cow contained lumps when coming out of the udder (FIGS. 3A and B). The crumbly milk comes out of the udder for several days, after which the cow starts producing normal milk again. Hereafter, the red infection color of the udder disappeared and the SCC strongly decreased in the weeks hereafter. The above described observations are an usual healing process of mastitis after administration of a PTSO/PTS tablet.

Example 5.5

The cell count is an important indicator for udder health and is measured to study the effect of a tablet that contains 3.84 g PTSO plus 0.96 gram PTS on the udder health. Two groups of 20 cows from two different farms are examined. The cows are selected when the cell count exceeds the limit of 250,000 cells/ml at the last or second to last MPR. Each cow of the study group is sampled before giving the PTSO/PTS tablet. After having received the tablet, the cow was sampled once every week and the sample was analyzed for somatic cell count during a period of three months and an analysis for cell count is carried out weekly over three months.

The average cell count for both farms measured weekly is listed in Table 16.

TABLE 16

Average cell count measured on Farm 1 and Farm 2 over the period of three months.

| Weeks | Cell counts-Farm 1 (×1000 cells/ml) | Cells count-Farm 2 (×1000 cells/ml) |
|---|---|---|
| 0 | 742 | 562 |
| 1 | 797 | 1487 |
| 2 | 988 | 1410 |
| 3 | 816 | 739 |

TABLE 16-continued

Average cell count measured on Farm 1 and Farm 2 over the period of three months.

| Weeks | Cell counts-Farm 1 (×1000 cells/ml) | Cells count-Farm 2 (×1000 cells/ml) |
|---|---|---|
| 4 | 1162 | 1102 |
| 5 | 530 | 676 |
| 6 | 409 | 936 |
| 7 | 201 | 738 |
| 8 | 169 | 292 |
| 9 | 180 | 312 |
| 10 | 273 | 200 |
| 11 | 242 | 403 |
| 12 | 206 | 389 |

The results from both farms indicate a rapid decrease in cell counts during the first approximately six weeks followed by gradual decrease after seven weeks. Which is in align with the expected effect of the dose. The conclusion was that after treatment with the first dose of the PTSO/PTS-tablet the cows with cell count higher than 250,000 cells/ml showed a significant decrease in cell count to approximately 250,000 cells/ml. From this example it was demonstrated that the effect on SCC decrease was remarkably long.

Example 5.6

Four individual farms and in total 47 cows were examined on the effect of a tablet that contains 3.84 g PTSO plus 0.96 gram PTS on SCC.

Study Design

Farm 1: 11 cows, in total 3 MPRs after first treatment.

Farm 2: 8 cows, in total 9 MPRs after first treatment.

Farm 3: 16 cows, in total 13 MPRs after first treatment.

Farm 4: 12 cows, in total 2 MPRs after first treatment.

More data on the farms is listed in Table 17.

TABLE 17

The data of farm 1-4.

| | Farm 1 | Farm 2 | Farm 3 | Farm 4 |
|---|---|---|---|---|
| Size of farm | 170 cows | 200 cows | 100 cows | 250 cows |
| Number of liters (average per cow per year) | 8,000 liters | 11,200 liters | 9,000 liters | 10,000 liters |
| Method of milking | Parlour milking | Robotic milking | Parlour milking | Rotary Milking |
| Access to the outdoors | Yes | Yes | Yes | Yes |

Results and Discussion

The average cell count of the milk of the individual farms is depicted in table 18.

TABLE 18

| | MPR 0 | MPR 1 | MPR 2 | MPR 3 | MPR 4 |
|---|---|---|---|---|---|
| average | 1856.787 | 707.5319 | 447.3261 | 225.3438 | 213.7727 |
| number of cow | 47 | 47 | 46 | 32 | 22 |

In all cases the SCC count is lowered after treatment. For Farm 2 and 3 multiple MPRs were available showing a steady low value of SCC. This indicates the effectiveness of the tablet on SCC reduction over a longer period of time.

Example 5.7

In one farm of 5,500 cows in Hanford, California, the somatic cell count and milk production stats were measured monthly to study the effect of a tablet that contains 3.84 g PTSO plus 0.96 gram PTS on udder health. Cows were selected based on various criteria as indicated below and treated as indicated below. The efficacy of the PTSO/PTS tablet vs. a control group in lowering SCC was tested.

The objectives were to investigate whether there were significant differences when the following groups were compared after treatment:

Lower total average SCC in PTSO/PTS treated group vs. control group

More cows under 200K in PTSO/PTS treated group vs. control group

More cows under 100K in PTSO/PTS treated group vs. control group

Firstly, the cows were categorized into the following groups:

Selection criteria for farm trials using PTSO/PTS to support subclinical high SCC cows Current SCC >200,000 (SCC>200)

Previous SCC >200,000 (PSCC>200)

1st and 2nd Lactation animals (LACT<3)

Times treated for mastitis (XMAST)<3

Not "Do Not Breed" cows

Not within 60 days of dry-off. DCC<145 (this means Days Carried Calf (the current length of gestation of currently pregnant animals). At least 2 months additional test days SCC data were needed so the cows were not dried off before we get the data.

Divided into two equal groups.

Sorted by Lactation, within Lactation sort by SCC, then assign group AABB, etc.

Equalized groups for Lactation, SCC, PSCC, XMAST, ECM (=Energy Corrected Milk. A formula that standardizes production volume based on fat and protein content of the milk. Used to compare cows/herds with different production and milk components. For example, it allows a very high production cow with low fat & protein to be compared to a lower production cow with high fat and protein), etc.

In total, 100 cows were selected, 50 cows were selected for treatment with one PTSO/PTO tablet and 50 cows were not treated and used for comparison (control). After 6 weeks the average SCC in the PTSO/PTS treated group (323K) was 38% lower than the control group (523K) and had significantly more cows under 200K SCC (24 cows treated versus 15 control cows) and under 100K SCC (13 cows treated versus 7 control cows).

Example 5.8

In three farms in The Netherlands, eighteen cows with elevated somatic cell counts (>200,000 cells/ml) indicating mastitis were selected to receive a tablet that contains 3.84 g PTSO plus 0.96 gram PTS. The somatic cell counts were measured three times at regular intervals of thirty days. Before treatment, the eighteen cows had an average somatic cell count that exceeded 600,000 cells/ml. By the first measurement, the average somatic cell count was below 300,000 cells/ml, a more that fifty percent improvement. At the second measurement date, the average for the group was below the 200,000 cells/ml threshold for a cow to be considered infected. The third round of measurements showed that the average had declined to under 100,000 cells/ml. These cows, formally labeled as having a high somatic cell count, are now producing milk that can command a premium.

Example 5.9

In a second trial taking place on another client dairy, the results of treatment with a tablet that contains 3.84 g PTSO plus 0.96 gram PTS were compared to cows that received a standard antibiotic dry cow treatment (control cows). Like Example 5.8, both groups consisted of cows who had initial high somatic cell counts. Nine cows were selected to receive PTSO/PTS tablets and 11 were selected to be studied as a control (see Table 19). The somatic cell counts of the participants were measured at regular intervals for a total of 3 data collections. At the first measurement date after treatment (MPR 1), 89 percent of PTSO/PTS-treated cows showed somatic cell counts under 150,000 cells/ml in comparison to 36 percent of the control group cows. At the fourth measurement, all PTSO/PTS-treated cows had lowered their somatic cell counts to below 150,000 cells/ml, compared to just 29 percent of conventionally treated cows.

TABLE 19

| | % treated below 150K SCC | % control below 150K SCC | p-value | No. cows treated | No. control cows |
|---|---|---|---|---|---|
| MPR 0 (before treatment) | 0 | 0 | | 9 | 11 |
| MPR 1 | 89 | 36 | 0.028 | 9 | 11 |
| MPR 2 | 89 | 18 | 0.005 | 9 | 11 |
| MPR 3 | 89 | 33 | 0.050 | 9 | 9 |
| MPR 4 | 100 | 29 | 0.021 | 7 | 7 |

Example 5.10

On four farms the change in somatic cell counts for cows with elevated test results was measured over time. Before treatment, selected Farm One cows (n=11) had an average somatic cell count of over 3,500,000 cells/ml, selected Farm Two cows (n=8) had an average somatic cell count of nearly 600,000 cells/ml, selected Farm Three cows (n=16) had an average somatic cell count of nearly 893,000 cells/ml, and selected Farm Four cows (n=12) had an average somatic cell count of 2,288,000 cells/ml. The cell counts were measured during monthly milk product registrations. The treatment with a tablet that contains 3.84 g PTSO plus 0.96 gram PTS (1 per cow) took place between MPR 0 and MPR 1. The average somatic cell count for the selected cows dropped significantly at all farms by MPR1. By MPR 3, 78% of all selected cows had a somatic cell count under 250,000 cells/ml. The average SCC for all cows was under 200,000 cells/ml at 4 months after treatment and remained under 200,000 cells/ml throughout the testing period (i.e., until at least 6 months after treatment).

Example 5.11

Effective Alternative to Traditional Dry Cow Therapy (DCT)

In an independent study performed at Waterford Institute of Technology, PTSO/PTS was tested as an alternative dry off treatment. 17 cows were treated with the PTSO/PTS tablet while sixteen cows received the traditional dry off treatment. The PTSO/PTS tablet contains 3.84 g PTSO plus 0.96 gram PTS and was administered 3 weeks prior to dry off. The control group received the conventional treatment on the same day, which included a usual antibiotic used for drying-off therapy. Comparing these two dry-off methods, 23.5% of the PTSO/PTS treated cows became infected, compared to 60% of traditionally treated cows. The cows were split into three groups: low somatic cell count cows (<200,000), medium somatic cell count cows (200,000-400,000) and high somatic cell count cows (>400,000). When the cows were categorized based on their somatic cell count prior to dry off, the PTSO/PTS treatment was successful in 92.9% (13 of 14 cows) of the low SCC cows, whereas the blanket DCT was only successful in treating 50% (6 from 12 cows) of this population. The results of the medium somatic cell count group were similar to the low somatic cell count cows. For the high somatic cell count cows, the PTSO/PTS tablet was an effective dry cow therapy in 50% (½) of cows, and comparably the blanket DCT was effective in 50% (1 of 2) of the cows. This included an outlier PTSO/PTS-treated cow who had a somatic cell count of 9,993,400 cells/ml. This cow showed a reduction of 146%, calving with a somatic cell count of 1,560,000 cells/ml, and she continued to have decreasing numbers over the next twelve weeks without further treatment.

Example 5.12

Research was performed by an external 3rd party clinic to evaluate the PTSO/PTS tablet. A total of 16 animals in 5 farms were monitored for changes in high cell counts after the administration of the tablet that contains 3.84 g PTSO plus 0.96 gram PTS. 14 animals completed the study. Over an average of 44, an average reduction in the number of cells by 45% (from 685,000 to 378,000) was demonstrated.

In addition, an evaluation of the pathogen detection and persistence in the individual quarters were carried out. 20 quarters with cell elevation from 19 cows from 6 farms were sampled and cultured. On Day 1, various pathogens (*Streptococcus uberis, Staphylococcus aureus, Escherichia coli*, etc.) were detectable in 12 quarters, and no pathogens were detected in 8 quarters. Of the 12 quarters with detected pathogens, on Day 42, pathogens were only detectable in 4 quarters and none in 8 quarters. This corresponds to a reduction of the pathogens by 67%.

Example 5.12

In a practical study to subclinical mastitis, carried out in Upper Bavaria, a total of 14 cows with mastitis were presented for changes with respect to the development of cell numbers before and after the administration of a tablet that contains 3.84 g PTSO plus 0.96 gram PTS. Furthermore, the presence and numbers of pathogens were examined after treatment at various time intervals in selected udder quarters.

Study Design

The cell count is an important indicator for udder health and is measured to study the effect of a tablet that contains 3.84 g PTSO plus 0.96 gram PTS on the udder health of 14 animals in 5 farms. The cows were selected when the cell count exceeds the limit of 250,000 cells/ml at the last or second to last MPR. The milk of each cow of the study group was sampled before giving the tablet. After the treatments, the cows were sampled at appropriate time intervals and the samples were analyzed for somatic cell counts and infected quarters in the udder. Furthermore, the microbial pathogenic specimens were identified and numbers were determined after appropriate time intervals.

Results and Discussion

In table 20 the results of the measurements are presented with respect to somatic cell counts, detected pathogens at various time intervals after treatment. Before treatment the cell counts were above 250,000/ml strongly indicating that an infection is present, and in most of the cows the numbers were rising. Treatment was provided between MPR−0 and MRP+1. After treatment, from the infections on t is 0 pathogen reduction was observed from 10 quarters with pathogen detection on day 1, to 7 quarters on day 14/15. Pathogens were still observed (reduction by 3 quarters, corresponding to 30%) and on day 42/43/44 the original pathogens were still detected in 3 quarters that corresponded to a reduction by 7 quarters (is 70%) of the originally infected quarters. However, in the time interval of the experiment 7 cows were infected with other pathogenic bacteria and these cows had to be retreated (results not shown). In all cows the somatic cell counts decreased on day 7 after the treatment. Since the SCC is a generally accepted measure for the level of inflammation, the treatment had a clear inhibiting effect on the inflammation. Interestingly, the SCC numbers were already significantly lowered on day 7 after the treatment and after 36-55 days, an average reduction in the number of cells by 45% (from 685,000 to 378,000 cells/ml) was demonstrated.

However, in most of the cases the pathogens were still detectable. Furthermore, clods of biofilm were leaving the udder from day 2 in a high rate and was (completely removed. This strongly indicated that biofilm is responsible for the inflammation, and not the planktonic cells that were still present in the udder. The number of planktonic cells decreased with time until they are not detectable any more, and this decrease can only be caused by the response of the action of the immune system. This demonstrated that removing the biofilm without killing the cells, is sufficient to control inflammation, and the immune system is responsible for controlling the infection.

TABLE 20

Development of somatic cell counts per cow and presence of pathogens per udder quarter after treatment with tablets that contains 3.84 g PTSO plus 0.96 gram PTS.

| Farm | cow number | MPR* −2 | MPR −1 | MPR −0 | MPR +1** |
|---|---|---|---|---|---|
| 1 | 1 | 70 | 137 | 456 | 382 |
| | 2 | 38 | 238 | 388 | 126 |
| | 3 | 195 | 356 | 366 | 264 |
| 2 | 4 | 25 | 40 | 2244 | 553 |
| | 5 | 292 | 1726 | 1320 | 1076 |
| | 6 | 31 | 262 | 733 | 491 |
| 3 | 7 | 173 | 1303 | 453 | 251 |
| | 8 | 233 | 423 | 403 | 342 |
| | 9 | 92 | 598 | 445 | 263 |
| | 10 | 93 | 123 | 407 | 275 |
| | 11 | 56 | 26 | 579 | 317 |
| 4 | 12 | 2540 | 749 | 502 | 348 |
| | 13 | n.r.*** | 577 | 636 | 224 |
| 5 | 14 | 369 | 466 | 658 | 374 |

*MPR (milk production record) × 1000;
**MPR on day 7

Furthermore, an evaluation of the pathogen (pathogen) detection or the pathogen persistence in the individual quarters was carried out. 20 quarters with cell elevation from 19 cows from 6 farms were examined (milk sample, cultural approach). On day 1, various pathogens (*Streptococcus uberis, Staphylococcus aureus, Escherichia coli* etc.) were detectable in 12 quarters, no pathogen detection in 8 quarters. Of the 12 quarters with detected pathogens on day 1, on day 42 pathogens were only detectable in 4 quarters and none in 8 quarters. This corresponds to a reduction of the pathogens by 67%.

From this experiment, it is clear that PTSO/PTS is absorbed by the intestines and transported to the milk glands. Hereafter, PTSO/PTS enters the biofilm (which can be considered a kind of "fortress" in which the bacteria hide) in concentrations that are sufficiently high that release of the biofilm takes place. Although, the exact mechanism by which the biofilm dissolution and detachment process takes place is unclear, it is surprising that the compounds cause such an effect.

Example 6 *Prototheca*

A very deadly variant of mastitis is caused by the biofilm forming microalgae *Prototheca* spp. (Conçalves et al., 2015, Dairy Sci 98 (6): 3613-3621. Valessa et al, Cienc. Rural vol. 49 no. 2 Santa Maria Feb. 28, 2019). Mastitis caused by *Prototheca zopfii* has been described in various countries and is increasing worldwide and represents a serious problem due to the inherent resistance to routine therapy of these microalgae (Pieper et al., 2012. J. Dairy Sci. 95:5635-5644). This resistance is associated with the ability to infect and survive in macrophages and to invade mammary tissue, making them responsible for a persistent infection with regular occurrence of *P. zopfii* in milk (Marques et al., 2006, J. Dairy Sci. 89:4202-4204). Furthermore, it is observed that they can form biofilms in the udder (Shahid et al. 2020, Sci Rep 10, 698).

Transmission of *Prototheca* spp. takes place between infected and healthy cows during milking, the regular and intensive treatment with antibiotics (Pieper et al., 2012), and lack of hygiene during premilking preparation of cows. Furthermore, *P. zopfii* survive in feces and contaminates every environment.

In the dairy environments, surfaces such as stainless steel, glass, rubber and polypropylene are contaminated by microorganisms. Subsequently, the microorganisms may multiply and produce biofilms on these surfaces (Davies, 2003. Nat. Rev. Drug Discov. 2:114-122).

The treatment of mastitis caused by *Prototheca* spp. with antibiotics produces only temporary improvement of infection with *Prototheca* spp. infections in vivo, and the causative agent is not eliminated (Costa et al., 1996. Mycopathologia 133:85-88). Therefore, culling cows infected with *P. zopfii* is one of the recommended, if not the only control measure to reduce the disease.

Scope: in a practical study to (sub)clinical mastitis, carried out in Upper Bavaria, a total of 14 cows with mastitis were presented for changes with respect to the development of cell numbers before and after the administration of a tablet that contains 4.8 g PTSO plus 1.2 gram PTS. Furthermore, the presence and numbers of *Prototheca* were examined after treatment at various time intervals in selected udder quarters.

Study Design

The cell count is an important indicator for udder health and is measured to study the effect of the PTSO/PTS tablet products on the udder health of 44 animals. The cows were selected when the cell count exceeds the limit of 250,000 cells/ml at the last MPR in the milk and the microalga *Prototheca* was demonstrated in the milk. Hereafter, the PTSO/PTS tablet was admitted. After the treatments, the cows were sampled once every month and the sample was analyzed for cell count and presence of the microalga *Prototheca* in the udder at the end of the experiment.

Results and Discussion

In table 21 the results of the measurements are presented with respect to numbers of somatic cell counts in time and the presence of *Prototheca* at the end of the experiment.

TABLE 21

Somatic cell counts (SCC) and SCC changes in time after treatment with the PTSO/PTS tablets and presence of Prototheca at the end of the experiment.

| Cow number | SCC t = 0 | SCC t = 1 month | SCC t = 2 months | SCC t = 1 minus SCC t = 2 | Prototheca test |
|---|---|---|---|---|---|
| 837 | 1146 | 3528 | 3012 | 516 | + |
| 4631 | 5011 | 3497 | 2975 | 522 | + |
| 4827 | 1877 | 3190 | 453 | 2737 | + |
| 4927 | 4358 | 671 | 2177 | −1506 | + |
| 4941 | 2190 | 3401 | 2151 | 1250 | + |
| 5027 | 2473 | 3997 | 3063 | 934 | − |
| 5083 | 3784 | 1162 | 3804 | −2642 | + |
| 5116 | 530 | 617 | 280 | 337 | + |
| 5147 | 542 | 488 | 414 | −74 | − |
| 5470 | 582 | 539 | 132 | −407 | − |
| 5485 | 1511 | 1059 | 383 | −676 | − |
| 5505 | 1109 | 5404 | 1491 | 3913 | + |
| 5544 | 246 | 197 | 124 | −73 | − |
| 5581 | 436 | 423 | 696 | −237 | − |
| 5586 | 4052 | 3994 | 2847 | 1147 | + |
| 5674 | 3370 | 2645 | 3649 | −1004 | + |
| 5706 | 3186 | 2552 | 640 | 1912 | + |
| 5807 | 931 | 1292 | 1152 | 140 | + |
| 5841 | 652 | 62 | 220 | −158 | + |
| 5880 | 1030 | 637 | 431 | 206 | − |
| 5889 | 1427 | 2027 | 352 | 1675 | − |
| 5916 | 1811 | 285 | 442 | −157 | − |
| 5945 | 1078 | 370 | 162 | 208 | − |
| 5998 | 2944 | 951 | 1433 | -482 | − |
| 6011 | 960 | 691 | 158 | 533 | − |
| 6026 | 1699 | 1386 | 1284 | 102 | + |
| 6041 | 4586 | 5176 | 7009 | −1833 | − |
| 6078 | 650 | 238 | 113 | 125 | − |
| 6081 | 2951 | 2627 | 1374 | 1253 | + |
| 6131 | 708 | 564 | 191 | 373 | − |
| 6140 | 1731 | 48 | 466 | −418 | − |
| 6152 | 1114 | 1479 | 1101 | 378 | − |
| 6181 | 1462 | 1366 | 2918 | −1552 | + |
| 6182 | 1901 | 2423 | 1821 | 602 | + |
| 6186 | 1209 | 1849 | 625 | 1224 | + |
| 6192 | 3522 | 5401 | 6439 | −1038 | − |
| 6195 | 3935 | 4432 | 2535 | 1897 | − |
| 6230 | 1528 | 895 | 487 | 408 | − |
| 6241 | 1892 | 1456 | 203 | 1253 | − |
| 6252 | 3211 | 3034 | 2802 | 232 | + |
| 6275 | 511 | 404 | 689 | −285 | − |
| 6282 | 522 | 1562 | 1312 | 250 | − |
| 6556 | 2438 | 3355 | 1745 | 1610 | − |

*MPR (milk production record) × 1000;
**MPR on day 7;
***:

Before treatment the cell counts were above 250,000 cells/ml strongly indicating that an infection is present and in most of the cows the numbers were rising. In all cows the somatic cell counts decreased on day 7 after the treatment. Since the SCC is a measure for the level of inflammation as a consequence of infection, the treatment had a clear inhibiting effect on the inflammation. Interestingly, the SCC numbers were already significantly lowered on day 7 after the treatment and after 36-55 days, an average reduction in the number of cells by 45% (from 685,000 to 378,000 cells/ml) was demonstrated.

Furthermore, an evaluation of the pathogen (pathogen) detection or the pathogen persistence in the individual quarters was carried out. 20 quarters with cell elevation from 19 cows from 6 farms were examined (milk sample, cultural approach). On day 1, various pathogens (*Streptococcus uberis, Staphylococcus aureus, Escherichia coli* etc.) were detectable in 12 quarters, no pathogen detection in 8 quarters. Of the 12 quarters with detected pathogens on day 1, on day 42 pathogens were only detectable in 4 quarters and none in 8 quarters. This corresponds to a reduction of the pathogens by 67%.

Infection of the udder by the microalga *Prototheca* generally results in culling of the cow because the alga is insensitive for most of the antibiotics. Unexpectedly, PTSO/PTS demonstrated to completely resolve the infection and culling was not necessary.

Example 7. Digital Dermatitis

Another category of chronical infections are wounds that are infected by biofilm-forming microorganisms. Once the wound is infected, the microorganisms start to form a biofilm that remains attached to the wounds. The production of microbial EPS (Extracellular Polymeric Substances) helps the biofilm to form a complex, three-dimensional structure within a few hours. These complex structures are resistant to defence mechanisms in the wound. When antibiotics are applied to attack bacteria, they may only partially eradicate the biofilm and the wound and underlying tissues remain infected. These biofilms are known to lead to chronic infections and non-healing wounds. In the United States, around 16 million new biofilm-based infections are diagnosed every year. Hence biofilms constitute a major obstacle to wound healing. Examples of such wounds infecting pathogenic microorganisms are bacteria (Gram positive bacteria, for example *Staphylococcus aureus*; Streptococci; gram negative bacteria, for example *Treponema* spp., *Escherichia coli, Yersinia pestis, Pseudomonas aeruginosa*; yeast/fungi, for example *Candida* spp (*albicans*), *Cladosporium herbarum, Trichosporium, Rhodosporidium, Malassezia.*

One example of a wound infection that has a negative effect on milk production of cows is digital dermatitis (Schlafer et al, 2008 Veterinary Microbiology 128, Issues 1-2: 118-125). Digital dermatitis (synonyms are hairy heel warts, strawberry foot rot, mortellaro disease, Italian foot rot, papillomatous digital dermatitis) is an infection that causes lameness with cattle. Digital dermatitis lesions are ulcerative or proliferative masses between the bulbs (Beninger, 2018 et al, Vet Res 49:111). Costs of digital dermatitis are $75 per cow per year for a farm of 65 cows (Bruijnis et al., 2010, J. of Dairy Science Volume 93, Issue 6, 2419-2432). Costs are based premature culling, milk loss and decreased fertility.

Digital dermatitis is caused by aerophilic or anaerobic bacteria (Beninger, 2018 et al, Vet Res 49:111) and in particular *Treponema* spp (Demirkan et al. 2018 J. of Dairy Science vol 101 (11) p. 10317-10326). Generally, the infection is started by *Treponema* spp. that penetrate the skin around the claws. *Treponema* spp. are anaerobic gram-negative bacteria and belong to the spirochaetes. These microorganisms are able to penetrate the skin of the cows nearby the claws, preferentially between the claw in the interdigital cleft. The biofilms that develop from these dermatitis lesions comprise a that a heterogenous microbiological community.

Bacteria, like *Treponema*, are present in cow pat or in the dung of ruminants and are considered the source for digital dermatitis. A cow with a well-functioning immunity system is less sensitive for digital dermatitis. Housing, hygiene, ventilation and nutrition are also important.

Formalin foot baths have a preventive effect on digital dermatitis and are often applied. However, from formalin it is known that it is unfavourable for health for the cow and farmer. If digital dermatitis is present on the claws, the claws must be thoroughly dried and cleaned after trimming, followed by disinfecting the claws in a foot bath once every two weeks. Furthermore, the affected skin is usually treated with an antibiotic-containing spray afterwards and in this manner positive results may be achieved. However, often in the wound a thin layer or spots of biofilm are formed in which microbial cells are present in a dormant state. Only a part of the bacterial population is killed by the (antibiotic) treatment whereas the remaining cells start to multiply after the treatment was ended. Furthermore, usually the infection penetrates deep in the corium skin where local biofilms are formed and the large molecules of the antibiotics have little effect. Moreover, a selective pressure is applied to other forms of antibiotic resistance than cell dormancy in tissue and biolayers. For those reasons, most treatments and strategies have little or no effect for ameliorating digital dermatitis.

Study Design

Experiments are performed on three individual farms to examine the effect of two sprays developed for treating wounds and injuries (Spray #1 and Spray #2-PTSO). Both sprays have the same composition, with the exception that Spray #2-PTSO also includes PTSO (3.2% PTSO w/w). 0.35 ml is sprayed on a wound per treatment.

Cows on 13 farms are selected on the presence of digital dermatitis. These cows with digital dermatitis were selected and scored on locomotion and their M-scores. To classify a digital dermatitis infection, 6 classes were described (Dopfer et al., 1997) (Berry et al., 2012). The description of the M-scores are as follows: M0, healthy; M1 (early stage), small red and sensitive but active inflammation, minimal injury 0-2 cm; M2, strawberry-like red and very sensitive injury with white epithelial edge and upright hair, so a very active inflammation >2 cm; M3 (healing stage), an ulcerative lesion covered by a scab; M4, alteration to a chronic ulcer; M4.1, a combination of M4 and M1, a chronic phase with swollen claw cleft. The locomotion scores are defined as following: 1, not lameness, walks with straight back; 2, slightly lameness, walks with a slightly bowed back; 3, strongly lameness and bowed back during standing and walking; 4, strongly lameness and bowed back during standing and walking, affected leg is only used for standing and 5, strongly lameness and bowed back during standing and does not stand on the leg any more, prefers lying.

Figure 4:
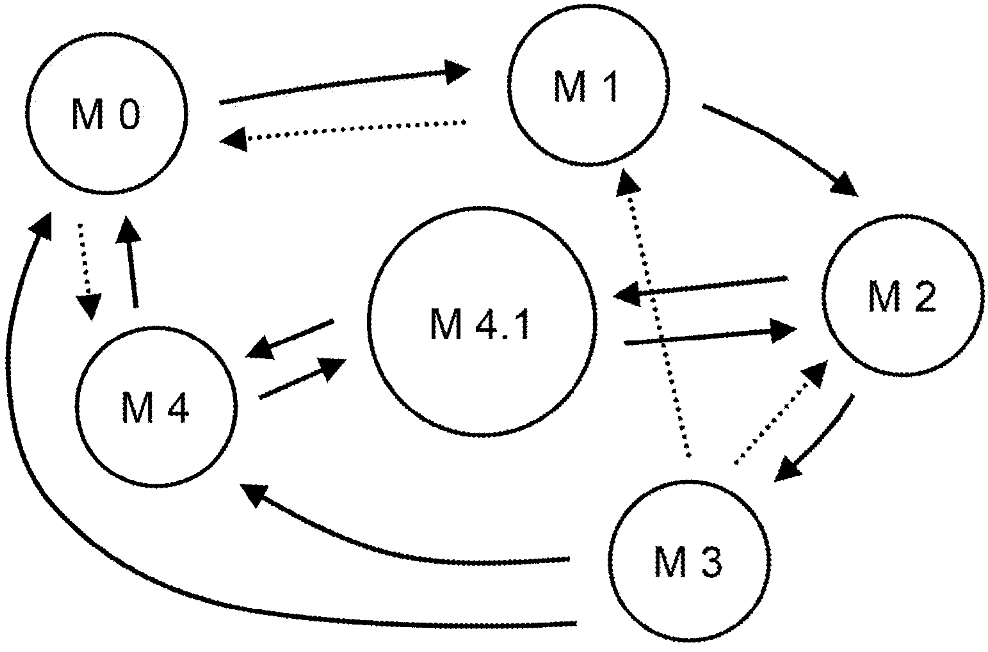
FIG. 4. Progress of infection (straight arrows) and healing (dotted arrows).

When an M2 lesion is treated, healing takes place as follows: an intermediate step (M3) leads to a healed stage (M0) or it turns into a chronic phase with swollen interclaw cleft (M4.1). The M4.1 heals via M4 to M3 after effective treatment. See, e.g., FIG. 4.

After scoring the wounds, the selected cows are randomly distributed over five groups as follows: Group 1: no treatment (control); Group 2: treatment with Spray #1; Group 3: treatment with Spray #2-PTSO; Group 4: treatment with Spray #1 and administration of a tablet that contains 4.8 g PTSO plus 1.2 gram PTS; and Group 5: treatment with Spray #2-PTSO and administration of a tablet that contains 4.8 g PTSO plus 1.2 gram PTS and treated with either Spray #1 or Spray #2-PTSO. The claws were scored on M-score and locomotion after two weeks. Each claw, if possible, was lifted up again and a picture was taken again.

Data Processing

Scores of cows were compared between Groups 1 and 3 and Groups 2 and 3. A Fisher's Exact Test was applied to calculate the statistical significance. M1, M2, M4 and M4.1 were considered as "not healed". M3 is indicated as "healing" and M0 for "healed". For the test "healing" and "healed" were combined.

Results

M scores per treatment group are shown in table 22. Most of the treated cows with an M4-score has a locomotion score of 1 or 2 before treatment with either spray. All of these cows have locomotion scores 1 after treatment, and the skin was after treating suppler. The cow from Group 5 scored 3 for locomotion, but directly after treatment it scored 2 for locomotion, so an immediate improvement was observed. Results on digital dermatitis were determined by M-scores. All cows with active (painful) lesions M1, M2 and M4.1 were moved to M3.

Cows that were treated with both the tablet that contains 4.8 g PTSO plus 1.2 gram PTS and Spray #1 showed that 93% of the M4 scores moved to M3 and the rest to M0 after treatment. When Spray #2-PTSO was used, the M2 scores of t=0 moved to M3. Cows with M4-scores moved to M0 (23%), M3 (56%) or remained in M4 (21%) after the treatment, so significant improvements were observed by use of Spray #2-PTSO whereas additional treatment with the PTSO/PTS tablet showed an additional effect. The control group showed higher M-scores because this group was not treated and the situation deteriorated as expected Most of the cows remained in the chronic group (M4).

TABLE 22

M-score prior before and after respective treatments.

| group | **0** | 1 | 2 | **3** | 4 | 4.1 |
|---|---|---|---|---|---|---|
| 1A | | 2 | | **5** | 26 | 9 |
| 1B | | | | **8** | 34 | |
| 2A | | 1 | 1 | **4** | 59 | 3 |
| 2B | **6** | | | **42** | 20 | |
| 3A | | 3 | 1 | **16** | 52 | 4 |
| 3B | **10** | | | **44** | 22 | |
| 4A | | | | | 6 | 3 |
| 4B | **1** | | | **7** | 1 | |
| 5A | | | 1 | **1** | 14 | 2 |
| 5B | **4** | | | **9** | 5 | |

M3 (bold) is indicated as "healing" and M0 for "healed" (bold).

Group 1: Control; Group 2: Spray #1; Group 3: Spray #2-PTSO; Group 4: Spray #1 plus PTSO/PTS tablet; Group 5: Spray #2-PTSO plus PTSO/PTS tablet. A indicates the number of cows with a particular M score prior to treatment and B indicates the number of cows with a particular score after treatment.

Statistical analysis was performed and the Fisher's Exact Test resulted in a P-value of 0.037 when comparing Groups 2 and 3 (i.e., spray with and without PTSO) and a P-value of 0.010 when comparing Group 1 to Group 3 (i.e., control versus spray with PTSO).

The health of the claws improved for both sprays, but the statistical P-value demonstrates that the spray comprising PTSO showed an improved effect over a similar spray without PTSO (p=0.032). Cows treated with Spray #1 showed better results when the treatment was combined with the PTSO/PTS tablet. The examples demonstrate that topical administration of PTSO is useful for the treatment of chronic biofilm-related wounds like digital dermatitis.

For cows treated with Spray #2-PTSO, we observed a larger impact on the infected stages M1 and M2 than for the chronic lesions (M4, M4.1). It is very plausible that further improvement is achieved by prolonging this treatment. One of the cows with a locomotion score 4 was treated, walks before treatment on 3 legs, the claw of the remaining leg was strongly affected by digital dermatitis that it could not be used. After treatment, the cow walks away on 4 claws and a locomotion score of 2 that clearly showed the pain killing effect of the treatment.

Example 8. Udder Cleft Dermatitis

Another example of a biofilm-related chronic wound is Udder Cleft Dermatitis (UCD) (Sorge et al, 2019. J. Dairy Sci. 102:11470-11475; Waller et al, 2014, J. Dairy Sci. 97:310-318). UCD is a skin lesion located at the anterior junction between the udder and the abdominal wall or between the front quarters of the udder. The lesions vary in appearance and size, but thickened skin, crusts, pus, and wounds that easily bleed are common findings. Udder cleft dermatitis can be difficult to detect due to its anatomical position and the fact that affected cows seldom show general signs of disease. Few studies on UCD prevalence have been published, and most have included only one or a few herds, mainly categorized as problem herds. The within-herd prevalence in those studies varied between 0 and 22%. In a recent Dutch study, however, 20 herds were included, of which 3 had no UCD, whereas the within-herd prevalence in the other herds varied between 2.5 and 13% (Amersfort et al., 2012). The etiology of UCD is unclear, but several factors, such as udder conformation and udder edema have been suggested to play a role. Cow factors such as parity and DIM (days in milk) have also been associated with UCD (Beattie and Taylor, 2000, J. Brit. Cattle Vet. Assoc. 8, 377-380).

Lesions are most commonly identified on the plantar aspect of the interdigital cleft of the hind limbs. *Treponema* spp are routinely present in large numbers of active lesions. Lesions are painful to the touch and can result in clinical lameness. The infectious nature generally results in endemic infection of cattle herds (Plummer et al 2017, Vet Clin North Am Food Anim Pract 33(2): 165-181) and is responsible for large economical loses.

Study design: Two cows were selected with clear characteristics of chronic UCD and were treated with the sprays described in Example 7. Cow 1 (3076) was treated with Spray #2-PTSO on day 0 and day 7. Cow 2 (2934) was treated with a Spray #1 on t=0 and Spray #2-PTSO at day 7. Tables 23 and 24 depict the results of treatment.

TABLE 23

| Wound description of cow 1 (3076) that was treated on day 0 and day 7. | | | |
|---|---|---|---|
| | Day 0 | Day 7 | Day 14 |
| Score | Inflamed, slimy and chronic wounds, sensitive, red colour, inflammatory moisture | Dry wound, not sensitive and not inflamed wound | Not inflamed and healing wound |

TABLE 24

| Wound description of cow 2 (2934) that was only treated at day 7. | | | |
|---|---|---|---|
| | Day 0 | Day 7 | Day 14 |
| Score | Chronic and slimy wounds, thick wound crusts, clearly inflamed, red and sensitive | Thick wound crusts, clearly inflamed, red and sensitive | Thin wound crusts, no inflammation, healing wound |

Cow 1 was treated at day 0 and day 7 with Spray #2-PTSO and inflammation reduction was observed immediately. No progress was observed when cow 2934 was treated with Spray #1 at day 0. After treatment with Spray #2 at day 7, a clear improvement was observed with respect to reduction of infection followed by wound healing. These experiments have been repeated with hundreds of cows and improvement and healing of the chronic slimy wounds of UCD by spray #2-PTSO has been observed.

The invention claimed is:

1. A method for treating a biofilm-related infection in an individual, said method comprising administering to an individual in need thereof a composition comprising a compound according to formula I Formula I

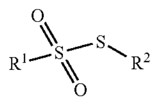

wherein R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl.

2. The method of claim 1, wherein the compound is propyl-propane thiosulfonate (PTSO).

3. The method of claim 1, wherein said method further comprises administering to an individual in need thereof a compound for use according to formula II Formula II

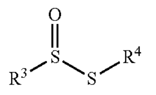

wherein R3 and R4 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula II is not

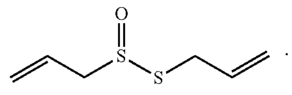

4. The method of claim 3, wherein the compound according to formula II is propyl-propane-thiosulfinate (PTS).

5. The method of claim 1, wherein said method further comprises administering to an individual in need thereof a compound having Formula III Formula III

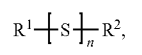

wherein n is 1, 2, or 3 and R1 and R2 are independently selected from optionally substituted linear or branched alkyl, optionally substituted linear or branched alkenyl, optionally substituted linear or branched alkynyl, optionally substituted aryl, optionally substituted cycloalkyl, optionally substituted heterocycloalkyl, provided that Formula III is not

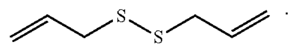

6. The method of claim 1, wherein said method further comprises administering to an individual in need thereof an antimicrobial agent and/or an anti-inflammatory agent.

7. The method of claim 1, wherein the biofilm-related infection is a chronic and/or persistent infection.

8. The method of claim 1, wherein the biofilm-related infection is digital dermatitis or a chronic wound infection.

9. The method of claim 1, wherein the biofilm-related infection is an infection of the mammary gland.

10. The method of claim 9, wherein the biofilm-related infection is mastitis.

11. The method of claim 1, wherein the individual is a mammal.

12. The method of claim 1, wherein the individual is a ruminant.

13. The method of claim 1, wherein the composition is substantially free of diallyl thiosulfinate.

14. The method of claim 1, wherein the biofilm comprises bacteria, yeast, fungi, microalgae, or a combination thereof.

* * * * *